United States Patent [19]

Sawai et al.

[11] 4,224,304

[45] * Sep. 23, 1980

[54] METHOD AND APPARATUS FOR THE MEASUREMENT OF ANTIGENS AND ANTIBODIES

[75] Inventors: Masanobu Sawai, Yamato; Tadamitsu Sudo, Sagamihara; Shogo Enomoto, Tokorozawa, all of Japan

[73] Assignee: Mitsubishi Chemical Industries, Limited, Tokyo, Japan

[*] Notice: The portion of the term of this patent subsequent to Oct. 3, 1995, has been disclaimed.

[21] Appl. No.: 917,251

[22] Filed: Jun. 20, 1978

Related U.S. Application Data

[63] Continuation-in-part of Ser. No. 825,160, Aug. 16, 1977, Pat. No. 4,118,192.

[30] Foreign Application Priority Data

Feb. 14, 1978 [JP] Japan .................. 53/15017

[51] Int. Cl.² ............... G01N 21/24; G01N 33/16
[52] U.S. Cl. ........................ 424/12; 23/230 B; 356/246; 422/55; 422/58; 435/7
[58] Field of Search ............ 23/230 B; 424/12; 195/103.5 A; 356/105, 246; 422/55, 56, 58; 435/7

[56] References Cited

U.S. PATENT DOCUMENTS

| | | | |
|---|---|---|---|
| 3,984,533 | 10/1976 | Uzgiris | 23/230 B |
| 4,011,044 | 3/1977 | Uzgiris | 23/230 B |
| 4,118,192 | 10/1978 | Sawai et al. | 195/103.5 A |

FOREIGN PATENT DOCUMENTS

2749956 5/1978 Fed. Rep. of Germany .
1384399 2/1975 United Kingdom .

OTHER PUBLICATIONS

R. J. Cohen, Immunochemistry, 12, pp. 349–351 (Apr. 1975).

Primary Examiner—R. E. Serwin
Attorney, Agent, or Firm—Oblon, Fisher, Spivak, McClelland & Maier

[57] ABSTRACT

A method of the quantitative measurement of antigens and antibodies by reacting antibody- or antigen-sensitized insoluble carrier particles with a corresponding antigen or antibody or a mixture thereof in a sample, irradiating the reaction mixture with light of a specific wavelength to measure the transmitted light at two or more points of time as the reaction proceeds, and then evaluating an increase in absorbance or percent absorption of the reaction mixture for a given period of time, and an apparatus for use therein.

34 Claims, 17 Drawing Figures

METHOD AND APPARATUS FOR THE MEASUREMENT OF ANTIGENS AND ANTIBODIES

CROSS-REFERENCE TO RELATED APPLICATIONS

This application is a continuation-in-part of application Ser. No. 825,160 of Aug. 16, 1977 now U.S. Pat. No. 4,118,192.

BACKGROUND OF THE INVENTION

1. Field of the Invention

This invention relates to a method and apparatus for the measurement of antigens and antibodies. More particularly, this invention relates to a method of the quantitative measurement of antigens and antibodies by supporting an antibody or an antigen on insoluble carrier particles having minute particle diameters to sensitize the insoluble carrier particles, then reacting the sensitized carrier with a corresponding antigen, antibody or mixture thereof and irradiating the reaction mixture with light of a specific wavelength to measure the transmitted light at two or more points of time, and then evaluating an increase in absorbance or percent absorption of the reaction mixture for a given period of time, and an apparatus for use therein.

2. Description of the Prior Art

There is a continuing need for rapid, accurate, qualitative and quantitative determinations of biologically active substances, e.g., antigens, antibodies, at extremely low concentrations. Today, there is a wide need for determining the presence of drugs in body fluids. In addition, in medical diagnosis, it is frequently important to know the presence of various substances which are synthesized naturally by the body or ingested.

Heretofore it has been known to detect antibodies or antigens semiquantitatively by reacting latex particles on which an antibody or an antigen is supported with a corresponding antigen or antibody on a glass plate and observing visually the agglutination state.

In recent years, it was proposed in the following articles to quantitatively determine antigens and antibodies using the above-mentioned latex particles by supporting the corresponding antibody or antigen on the latex particles to sensitize the latex, reacting the supported antibody or antigen with the antigen or antibody to be determined to agglutinate the latex particles, and measuring the rate of decrease in turbidity of the supernatant of the latex by means of visible lights for the determination of the antigen or antibody utilizing the agglutination phenomena of the latex reagent:

(A) CROATICA CHEMICA ACTA, 42, (1970), p.p. 457-466; and (B) European Journal of Biochemistry, Vol. 20, No. 4, (1971), p.p. 558-560.

Since the method of the above proposal utilizes the measurement of rate of decrease in turbidity to determine the antigen or antibody, it is necessary to use an antibody- or antigen-sensitized latex of an extremely low concentration, for example, in the range of 0.007 to 0.028%, to carry out the reaction of the latex and the antigen or antibody in a stationary state, to remove any impurity capable of affecting the turbidity from the sample to be tested, and the like. As a result, the above-mentioned method is disadvantageous in that the rate of the antigen-antibody reaction is inevitably decreased, both the precision and the reproducibility are insufficient for the determination technique of antigens or antibodies, and that the removal of impurities sometimes requires extremely complicated operations. Accordingly it is difficult to apply the above method to the determination of such antigen as fibrinogen (Fg), human chorionic gonadotropin (hCG) or the like, since it requires complicated procedures for the preparation of its reagent and it is difficult to cause reproducible agglutination reaction if it is present in blood or urine which also contains various other substances capable of adversely affecting the reaction.

Also in the article, (C) Immunochemistry, Vol. 12, p.p. 349-351 (1975) it was proposed to determine quantitatively antibodies and antigens by irradiating the above-mentioned agglutinated latex particles with a laser beam and measuring the change in width of spectral lines of the scattered light of the laser beam in order to determine the mean diffusion constant $(\overline{D})$ which gives an indication of the Brownian motion of the agglutinated particles which in turns is inversely proportional to the size of the agglutinated particles. Also in this method, since the antibody- or antigen-sensitized latex is used in an extremely low concentration, for example, as low as 0.001%, the rate of the antigen-antibody reaction is so decreased that both the precision and the reproducibility become poor. In addition, this method is also disadvantageous in that it requires complicated calculation using the technique of spectrum analysis which in turn requires complicated operations, and that any impurity in the sample must be removed prior to the measurement. Accordingly, this method has not been put into practice as well.

The above paper C also describes that determination by the turbidity method as reported in the foregoing paper A gives extremely imprecise results (FIG. 2 on page 350 of the same).

As a result of our investigation with respect to methods and apparatus for the rapid determination of an antigen and/or antibody in a sample to be tested with a high precision and a good reproducibility, we formerly accomplished an invention which is the subject matter of Japanese Patent Application No. 97158/76 (hereinafter referred to as "our prior filed application").

The invention of our prior filed application above resides in a method for measuring antigens and antibodies comprising supporting an antibody or antigen corresponding to the antigen or antibody to be determined on insoluble carrier particles having an average diameter of not greater than 1.6 microns, reacting the supported antibody and/or antigen with the antigen or antibody or a mixture thereof to be determined and irradiating the reaction mixture with light having a wavelength in the range of 0.6 to 2.4 microns and longer than the average diameter of said carrier particles by a factor of at least 1.5 to determine the absorbance of the reaction mixture.

SUMMARY OF THE INVENTION

Upon our further investigation for the purpose of providing an improvement over the invention of our prior filed application, we have now found that a reproducible, rapid determination of antigens and antibodies can be realized with higher precision by measuring the apparent rate of an antigen-antibody reaction in terms of the rate of increase in absorbance or percent absorption thereof for light in the above-mentioned near infrared region applied to the reaction mixture and accomplished this invention.

Thus, in accordance with this invention, there is provided a method capable of highly accurate, rapid determination of antigens and antibodies, which comprises reacting an antigen or antibody or a mixture thereof in a liquid medium with the corresponding antibody and/or antigen which has been supported on insoluble carrier particles having an average diameter of not greater than 1.6 microns to sensitize the carrier particles, irradiating the reaction mixture with light having a wavelength or wavelengths in the range of 0.6 to 2.4 microns to measure the transmitted light at two or more points of time as the reaction proceeds, and then evaluating an increase in absorbance or percent absorption of the reaction mixture for a given period of time.

Also, in accordance with this invention, there is provided an apparatus useful for the practice of the above method.

The apparatus according to this invention involves:

(a) insoluble carrier particles for supporting an antibody or antigen which corresponds to an antigen or antibody to be determined, said carrier particles having an average diameter of not greater than 1.6 microns;

(b) an absorption cell for holding the reaction mixture of an antibody or antigen supported on the insoluble carrier and an antigen or antibody or a mixture thereof to be determined in a liquid medium, said cell having a thickness of 0.5 to 10 mm;

(c) an irradiation unit for applying a light or lights of wavelengths in the range of 0.6 to 2.4 microns;

(d) a means for sensing the intensity of the light of a wavelength or wavelengths in the range of 0.6 to 2.4 microns applied to the reaction mixture in the absorption cell and transmitted thereby; and (e) a means for evaluating the change of absorbance or percent absorption of the reaction mixture for the light of the wavelength sensed in step (d) as a function of the reaction time, said evaluating means being operated in response to the sensing means.

DETAILED DESCRIPTION OF THE PREFERRED EMBODIMENTS

Figure 1:
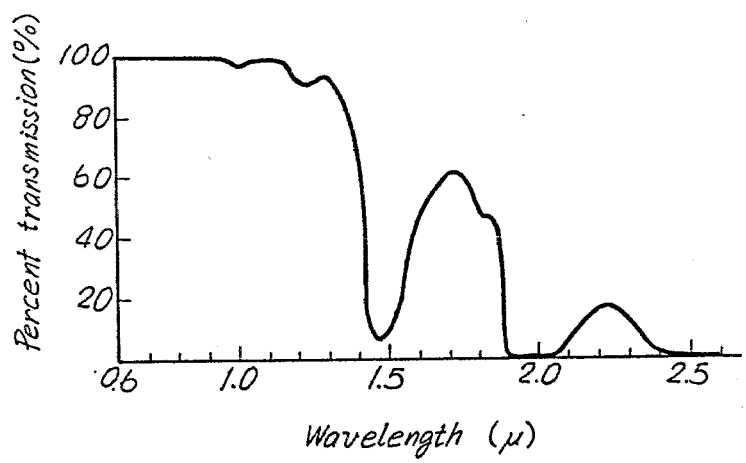
FIG. 1 is a chart of the absorption spectrum of water in the wavelength range of the applied light of 0.6 to 2.4 microns measured with an absorption cell of 1 mm in thickness.

In accordance with the method and apparatus of this invention, an extremely small amount of an antigen and/or antibody which could heretofore be determined practically only by the radioimmunoassay (RIA) method can be determined with a precision equal to or higher than that of the RIA method and much more rapidly and safely.

Also, in accordance with the method and apparatus of this invention, it is possible to determine not only multivalent antigens, but incomplete antigens such as, for example, haptens with high precisions, and the antigens and/or antibodies can be determined not only through their agglutination reaction, but through their agglutination inhibition.

Other objects and advantages of this invention will become apparent from the following more detailed description of this invention.

As previously mentioned, in one aspect, this invention resides in a method for quantitatively determining antigens and antibodies, comprising, reacting an antigen or antibody or a mixture thereof in a liquid medium with the corresponding antibody and/or antigen which has been supported on insoluble carrier particles having an average diameter of not greater than 1.6 microns to sensitize the carrier particles, irradiating the reaction mixture with light having a wavelength or wavelengths in the range of 0.6 to 2.4 microns to measure the transmitted light at two or more points of time as the reaction proceeds, and then evaluating an increase in absorbance or percent absorption of the reaction mixture for a given period of time.

As is obvious from the above description, by the term "reaction mixture" used herein is not meant a reaction mixture in which an antigen-antibody reaction has been completed, but by this term is meant a reaction mixture in which the reaction is in progress. Thus, the determination according to this invention is characterized by measuring the apparent reaction rate of such a reaction mixture in which an antigen-antibody reaction is in progress in terms of the rate of increase in absorbance or percent absorption of the reaction mixture for light in the above-mentioned near infrared region or a portion of the visible region nearest to the near infrared region.

As previously mentioned, the prior art method in which the degree of agglutination resulting from contact of a sample containing an antigen or antibody or a mixture thereof with latex particles on which the corresponding antibody and/or antigen has been supported (such latex particles herein after referred to as "sensitized carrier" or "sensitized latex") is evaluated by the rate of decrease in turbidity of the supernatant of the latex, involves various disadvantages such as poor precision and reproducibility, since the reaction has to be carried out in a stationary state with an extremely dilute latex. Also in this prior art method, it is necessary to previously remove any impurity in the sample which may affect the turbidity. In accordance with this invention, contrary to the above prior art method, it is desirable to carry out the reaction of an antigen or antibody in a sample with a sensitized latex in a moving state, preferably with agitation, and the reaction can be effected at a high concentration.

When an antigen or antibody in a sample is reacted in the presence of at least liquid medium with an insoluble carrier having an average diameter of not greater than 1.6 microns which has been sensitized with the corresponding antibody or antigen (sensitized carrier), at least at an initial state in the antigen-antibody reaction, particularly in a relatively early period thereof, the agglutination of the sensitized latex progresses as the reaction proceeds. Then, if the reaction mixture is irradiated with light of an appropriate wavelength or wavelengths in the range of 0.6 to 2.4 microns, the absorbance or percent absorption of the reaction mixture increases as the agglutination progresses. Thus, in accordance with this invention, the light to be applied to the reaction mixture may have any wavelength in the range of 0.6 to 2.4 microns as long as the absorbance or percent absorption of the reaction mixture increases in that wavelength region as the antigen-antibody reaction proceeds. Such proper wavelength region of light for a particular antigen or antibody in a sample and a particular sensitized carrier can be easily selected by preliminary experiments.

The light used in this invention may be either monochromatic or polychromatic light which has an appropriate wavelength or wavelengths in the range of 0.6 to 2.4 microns.

In fact, as hereinafter illustrated by the examples, it is possible in the practice of this invention to use relatively narrow polychromatic light having a half width of 35 nm or 55 nm, as well as, polychromatic light of extremely wide wavelength interval such as the light emitted from a tungsten lamp from which rays of wavelengths not more than about 800 nm (0.8 micron) are shielded.

The light used in this invention may consist essentially of rays of wavelengths in the range of 0.6 to 2.4 microns, or it may contain rays of wavelengths out of this range. In the latter case, the measurement of absorbance or percent absorption should be taken for light rays of wavelengths in the range of 0.6 to 2.4 microns as defined in the appended claims.

Preferably, the monochromatic or polychromatic light used in this invention has a wavelength or wavelengths in the range of 0.8 to 1.4 microns.

As mentioned above, the irradiating light used in this invention may contain spectral components other than those of wavelengths in the above-defined range, as long as it comprises a polychromatic light. As previously mentioned, the essential feature of such cases where the irradiating light used comprises a polychromatic light is that the measurement of absorbance or percent absorption should be taken for only such polychromatic light rays of the irradiating light as to have a particular wavelength region in the range of 0.6 to 2.4 microns and give an increase in absorbance or percent absorption by the lapse of time when applied to an antigen-antibody reaction mixture.

Thus, if the irradiating light consists essentially of these polychromatic light rays, the measurement of absorbance or percent absorption of a reaction mixture can be carried out without any treatment. On the contrary, if the light source for use in irradiation emitts light which additionally contains spectral components other than the above-mentioned polychromatic light rays, the measurement of absorbance or percent absorption may be carried out in the following manner:

(i) The light emitted from the light source is previously filtered or monochromated and only the selected portion of the light which consists essentially of the above-defined polychromatic light rays is applied as an irradiating light to the reaction mixture to measure the absorbance or percent absorption;

(ii) The light emitted from the light source is directly applied to the reaction mixture as an irradiating light, the transmitted light is then filtered or monochromated and the selected portion of the transmitted light which consists essentially of the above-defined polychromatic light rays is measured to determine the absorbance or percent absorption; or (iii) The light emitted from the source is directly applied to the reaction mixture as an irradiating light, and by the use of a special light sensor which responds substantially only to the above-mentioned polychromatic light rays, only the portion of the transmitted light which consists essentially of these polychromatic light rays is measured to determine the absorbance or percent absorption.

Thus, the irradiating light may contain spectral components other than the above-mentioned polychromatic light rays or in other words it may contain spectral components having wavelengths beyond the range of 0.6 to 2.4 microns. However, these spectral components of wavelengths beyond the range of 0.6 to 2.4 microns do not essentially contribute to the measurement of absorbance or percent absorption in the method according to this invention and, in some cases, may cause even an adverse effect such as chemical changes of the reaction mixture, elevation of temperature, unexpected luminescence phenomenon or the like. It is generally undesirable, therefore, that the irradiating light contains a considerably large amount of such spectral components having wavelengths beyond the range of 0.6 to 2.4 microns, particularly ultraviolet rays and visible rays of wavelengths shorter than that of blue light. Preferably the irradiating light is substantially free from those rays having wavelengths shorter than 0.6 micron, more preferably shorter than 0.8 micron. On the other hand, since those rays having wavelengths longer than 2.4 microns tend to cause a rise in temperature of the reaction mixture, it is desirable that the irradiating light does not contain a significant amount of these longer wavelengths and preferably is substantially free from such longer wavelengths.

Particularly suitable irradiating light for use in this invention is either composed predominantly of polychromatic light rays having a wavelength range of 0.6 to 2.4 microns, preferably 0.8 to 1.4 microns or consists essentially of a monochromatic light ray having a wavelength in the same range.

By the term "polychromatic light" used herein is meant any compounded light consisting of a plurality of substantially monochromatic light rays or a continuous spectrum or a combination thereof. It is desirable that the polychromatic light has a wavelength range of 0.6 to 2.4 microns, preferably 0.8 to 1.4 microns. The half width or wavelength range of the polychromatic light is not critical, but it is generally preferred that the polychromatic light have a half width or wavelength range of at least 0.03 micron, more preferably at least 0.05 micron.

Thus, any light source capable of emitting the irradiating light as described above in detail may be used in irradiation. Exemplary of these light sources are tungsten lamps, xenon lamps, halogen lamps, the Nernst glower, nichrome heating wires, light emitting diodes (LED) and the like. Among these, tungsten lamps, halogen lamps, xenon lamps and the Nernst glower which are the sources of continuous spectra ranging over the visible and infrared regions are suitable sources, since an irradiating light of a wide wavelength range which is substantially free from rays of wavelengths lower than, for example, 0.8 micron can be readily obtained from the light emitted from these sources, merely by passing it through a low pass filter. The light emitting diodes, for example, Ga-As light emitting diodes have a maximum emission wavelength at about 0.95 micron with a half width of about 50 nm and are particularly useful sources since the emitted light can readily be used as the irradiation light of polychromatic type without any filtration or monochromating. If it is desired to get a monochromatic light from these sources, the irradiating light or transmitted light can be subjected to filtration or monochromating.

Heretofore the technique of spectrum analysis using a ray in the infrared region of wavelengths of at least 2.5 microns or a ray in the ultraviolet region of wavelengths of not greater than 0.4 micron is known as one method for investigating molecular structures or characteristics thereof. The rays in the near infrared or the adjacent visible region in the range of 0.6 to 2.4 microns which is used in this invention and which may hereinafter be referred to as "rays in the near infrared region" for the sake of convenience, however, have heretofore been considered to have only limited uses and therefore attracted little attention.

According to our investigation, it has been found that the above-mentioned rays in the near infrared region in principle possess eligibility as the light to be used in this invention, since they are transmitted very well by aqueous media such as water, aqueous solutions and the like which are used most generally as the basal media for the antigen- or antibody-containing samples such as water, sera, urine, salt solutions, etc., as well as, as the basal media for the above-mentioned latices and among these, particularly the rays in the near infrared wavelengths of from 0.8 to 1.4 microns and from 1.53 to 1.88 microns are absorbed by the aqueous media only to a very little extent.

Any of insoluble carrier having an average diameter of not greater than 1.6 microns can be used in this invention. Those insoluble carrier particles having an average diameter greater than 1.6 microns are unfavorable for the determination according to this invention, since it is difficult to keep a latex containing such particles stable. Preferably the insoluble carrier particles have an average diameter in the range of 0.1 to 1.0 micron, more preferably 0.2 to 0.8 micron, most preferably 0.2 to 0.6 micron.

In accordance with this invention, an antigen or antibody in a sample is reacted in the presence of at least liquid medium with insoluble carrier particles having an average diameter in the above-defined range which have been sensitized with the corresponding antibody or antigen (i.e., sensitized carrier) and the reaction mixture is irradiated with the above-mentioned light having an appropriate wavelength or wavelengths in the range of 0.6 to 2.4 microns after the reaction has been started. In such cases, the rate of increase in absorbance or percent absorption of the reaction mixture for the above-mentioned light is correlated very well to the apparent reaction rate of the antigen-antibody reaction, particularly at an early or middle stage in the reaction, and the apparent reaction rate is in turn correlated to the concentration of the antigen or antibody in the sample. On the basis of these principles, therefore, it is possible to determine the concentration of the antigen or antibody in the sample.

The term "percent absorption" used herein is defined by the equation:

$$S = \frac{I_o - I}{I_o} \times 100 \, (\%) \qquad (1)$$

wherein S represents percent absorption, $I_o$ represents the intensity of the transmitted light when the cell contains the same system as the reaction mixture to be measured except that the system is free from the antigen and/or antibody and I represents the intensity of the transmitted light when the cell contains the reaction mixture.

As is apparent from the above definition, the percent absorption used herein can be referred to, in another way, as the percentage of the light not transmitted by the reaction mixture or the percentage of the attenuated light.

The above-defined percent absorption is correlated to the value of absorbance (A) which can be obtained, for example, with a spectrophotometer generally for use in infrared spectrometry, and therefore it may be expressed in terms of such absorbance for the sake of convenience. In the infrared spectrometry, absorbance (A) is defined by the equation:

$$A = \log \frac{I_o}{I} \qquad (2)$$

wherein $I_o$ and I have the same meanings as defined in Equation (1).

Thus, in accordance with this invention, it is possible to determine antigens and antibodies utilizing either the percent absorption defined by Equation (1) or the absorbance defined by Equation (2), and by the use of either parameter, the data obtained will agree with each other in a reasonable, reliable range as long as the measurements are carried out properly.

In accordance with this invention, an antigen or antibody or a mixture thereof is reacted with the above-mentioned sensitized carrier in a liquid medium under predetermined, substantially fixed conditions and the rate of increase in absorbance or percent absorption of the reaction mixture per unit time is evaluated at a substantially fixed time after the reaction has been started, whereby the antigen or antibody can be determined quantitatively. After the reaction of the reactants, i.e., the sensitized latex and the antigen or antibody or a mixture thereof (or a reaction product thereof) has been started, the measurements for the evaluation of the above rate of increase in absorbance or percent absorption per unit time are desirably taken at the earliest at such period that the antigen-antibody reaction of the reaction mixture has come to a steady state. In this way more precise and reproducible results in measurements can be obtained.

For this purpose, the sensitized latex is brought into contact with and mixed with the test fluid containing the antigen or antibody, preferably with agitation, and the measurement of absorbance or percent absorption of the reaction mixture should not be taken immediately, but at the earliest, for example, 2 to 3 seconds, preferably about 5 seconds after the reactants have been mixed.

After the reaction of the sensitized latex and the antigen or antibody in the test fluid has been started in this way, the antigen-antibody reaction occurring in the reaction mixture soon comes to a steady state. At this stage, particularly at its early period when the reaction is in steady state, the absorbance or percent absorption of the reaction mixture increases almost steadily. Therefore, in the practice of this invention, it is advantageous to previously select such stage or period in the reaction course which shows a steady increase in absorbance or percent absorption by a preliminary experiment for a particular reaction mixture and subsequently to determine at the selected stage the antigen or antibody in a test fluid containing the antigen or antibody or a mixture thereof in unknown concentration.

It is a matter of course that in taking measurements the reaction between the sensitized latex and the test fluid be carried out under predetermined, substantially fixed conditions.

In the practice of this invention, it is advantageous to react the sensitized carrier with an antigen or antibody in a test fluid under substantially fixed conditions and then determine the rate of increase in absorbance or percent absorption of the reaction mixture at such stage that the absorbance or percent absorption shows an almost steady increase for the first time after the reaction has been started, whereby it is possible to accomplish the quantitative determination of antigens and antibodies with higher precision in a shorter time.

Also in the practice of this invention, it is convenient to react the sensitized latex with an antigen or antibody in a test fluid under substantially fixed conditions, then measure and store the absorbance or percent absorption of the reaction mixture at two or more points of time and evaluate the rate of increase in absorbance or percent absorption per unit time from the stored values of absorbance or percent absorption.

The determination of antigens and antibodies according to this invention may be carried out, for example, as follows:

First, an insoluble solid carrier (latex) having a certain average diameter is sensitized with a certain antibody or antigen which corresponds to an antigen or antibody to be determined. On the other hand, using the same antigen or antibody (or a mixture thereof) as that present in a sample solution to be actually tested, a set standard sample solutions which contain the antigen or antibody in various known concentrations in a liquid medium exactly or almost identical to that of the actual sample solution are prepared.

Subsequently the sensitized latex and one of the standard sample solutions as prepared above are admixed and the absorbance or percent absorption of the reaction mixture is determined with the progress of the antigen-antibody reaction after the progress of this reaction has reached a steady state.

Figure 3:
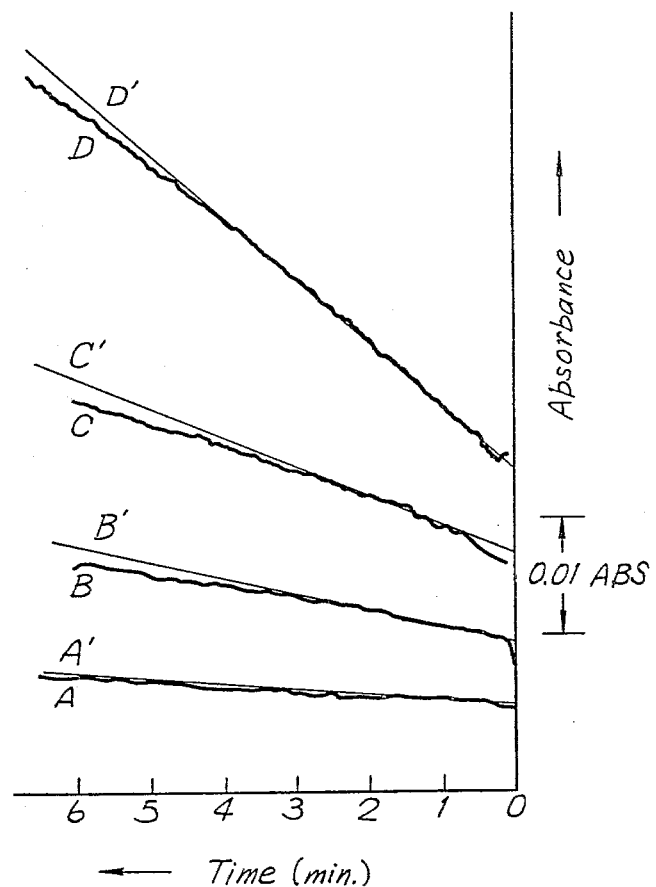
FIG. 3 is a chart which shows the change of absorbance with time for light of 950 nm recorded with the progress of the reaction which is caused by adding each of standard Fg solutions of various concentrations to a mixture of polystyrene latices having average diameters of 0.091 and 0.220 micron sensitized with an anti-(human fibrinogen) antibody.
Figure 5A:
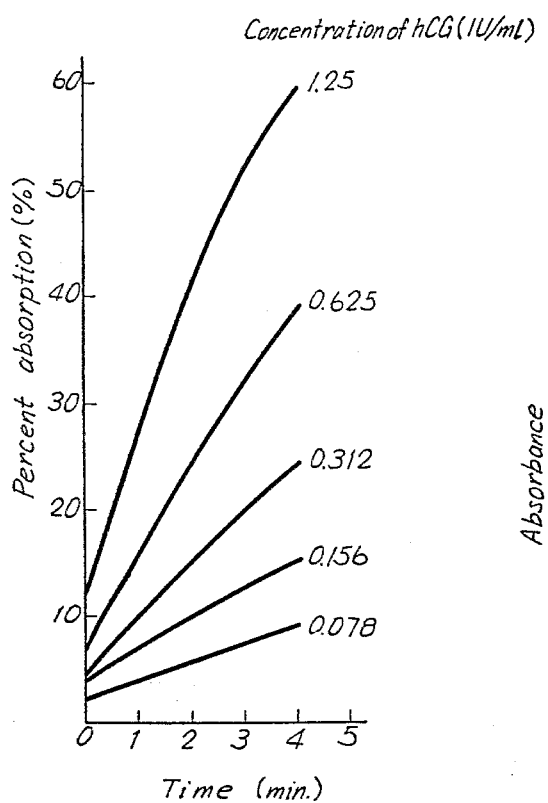
FIG. 5(a) is a chart which shows the change of percent absorption with time at a peak emission wavelength of 940 nm recorded with the progress of the reaction which is caused by adding each of standard hCG solutions of various concentrations to an anti-hCG-sensitized latex reagent.
Figure 5B:
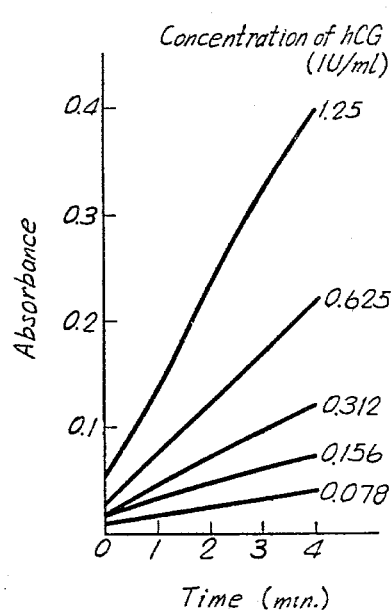
FIG. 5(b) is a graph derived from FIG. 5(a) by converting the percent absorption into the absorbance.

For example, in FIG. 3 (Example 1) and FIG. 5(a) and 5(b) (Example 2) of the accompanying drawing, the change (increase) in absorbance or percent absorption of some reaction mixtures with time is plotted, with time (minute) as abscissa and absorbance (for FIG. 3 and FIG. 5(b)) or percent absorption (for FIG. 5(a)) as ordinate. Among these, the curves designated as A, B, C and D in FIG. 3 provide a chart obtained by actually measuring the change (increase) in absorbance with time by means of a spectrophotometer for use in absorbance determination.

It is noted from these Curves A, B, C and D that, when a sensitized carrier and a standard sample solution are reacted, a steady state in the progress of the antigen-antibody reaction appears in its relatively early stage after the starting of the reaction and that particularly the initial portion of this stage shows an almost steady increase in absorbance or percent absorption of the reaction mixture.

In the practice of this invention, for each of the standard sample solutions, the rate of increase in absorbance or percent absorption of the reaction mixture per unit time is advantageously evaluated at such a stage or period that the absorbance or percent absorption increases almost steadily with time.

The rate of increase in absorbance or percent absorption may be determined, for example, for each of Curves A, B, C and D in FIG. 3, by evaluating the rate of increase in area between the curve and the base line (abscissa) for a fixed period of time (e.g., one minute) in a relatively linear portion of the curve. Alternatively, a straight line may be drawn through several plots in the relatively linear portion as indicated by A', B', C' or D' and the tangent of the angle ($\theta$) of inclination is determined for each straight line A', B', C' and D'.

Figure 4:
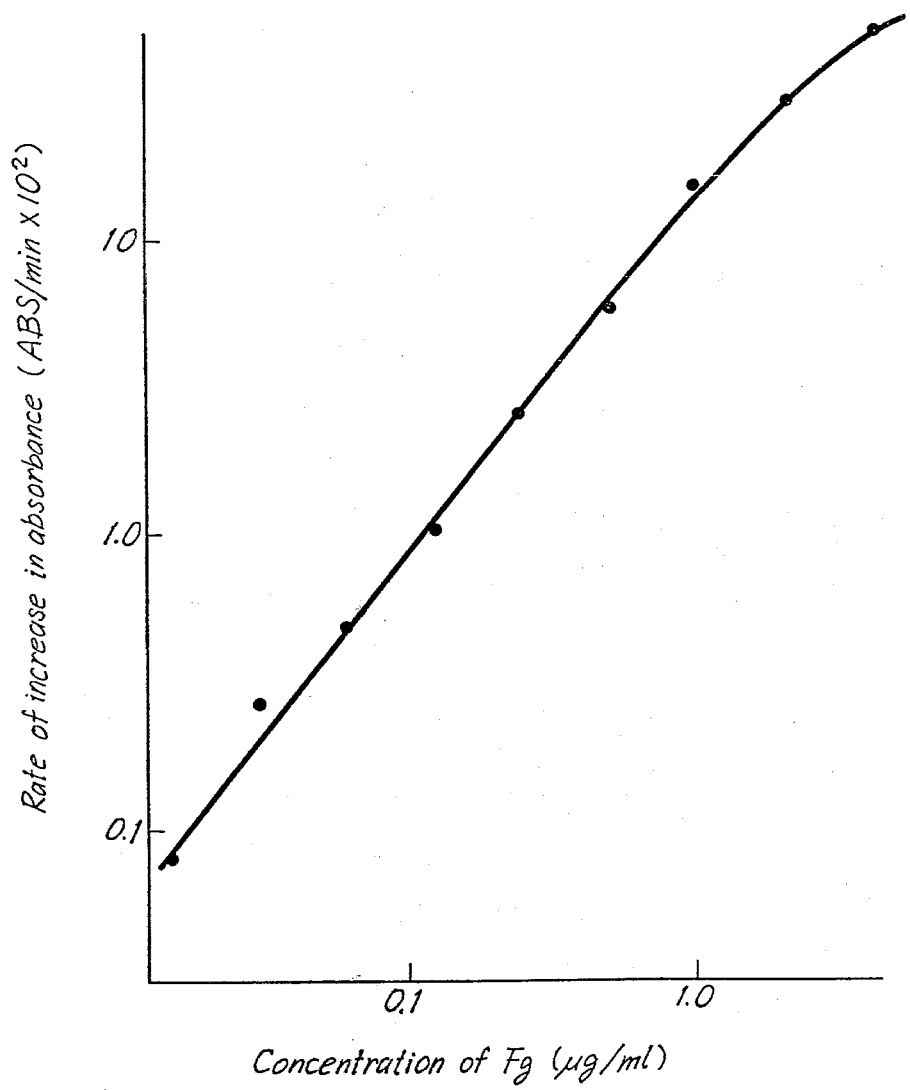
FIG. 4 is a graph which shows the relationship between the rate of increase in absorbance obtained from FIG. 3 and the concentration of standard Fg solution.
Figure 6A:
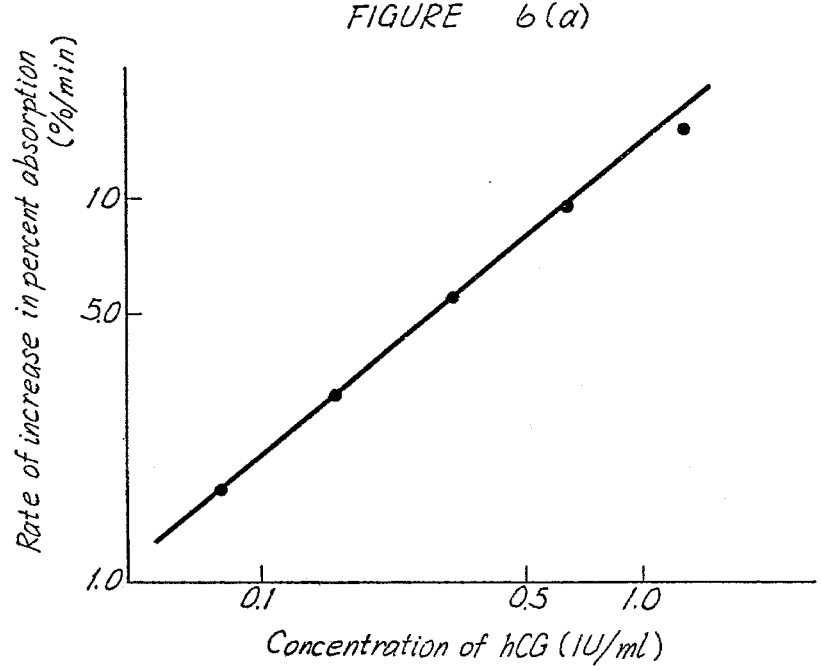
FIG. 6(a) is a graph which shows the relationship between the rate of increase in percent absorption obtained from FIG. 5(a) and the concentration of standard hCG solutions.
Figure 6B:
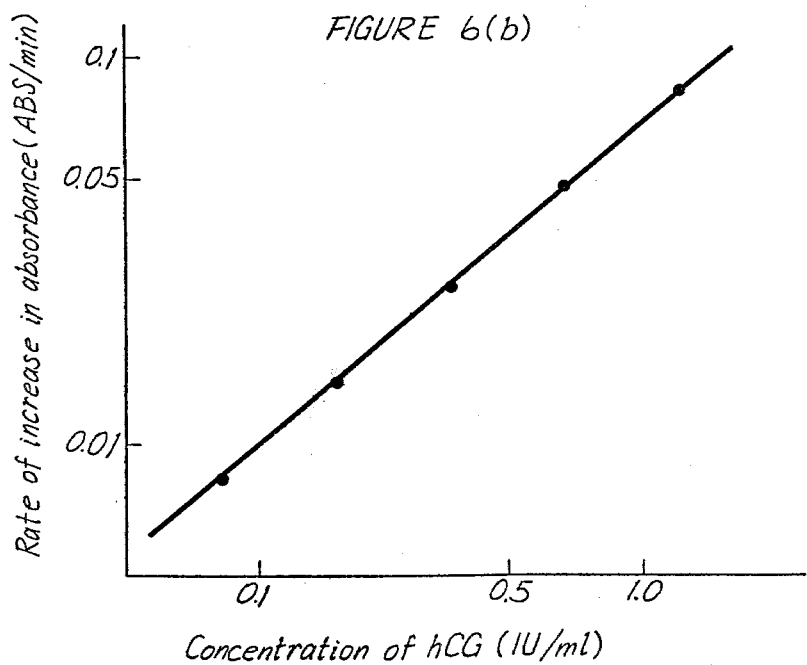
FIG. 6(b) is a graph which shows the relationship between the rate of increase in absorbance obtained from FIG. 5(b) and the concentration of standard hCG solutions.

Subsequently, the rate of increase in absorbance or percent absorption per unit time determined with each sample solution is plotted, for example, as ordinate (on a log scale) against, for example, the concentration of antigen or antibody in the standard sample solution plotted as abscissa (on a log scale). In this way, a graph (i.e., calibration curve) illustrated in, for example, FIG. 4 or FIG. 6(a) or 6(b) is derived. As can be seen from these graphs, the calibration curves indicate that an approximately linear relationship exists between the concentration of antigen or antibody in standard sample solution and the rate of increase in absorbance or percent absorption of the reaction mixture per unit time. Thus, the method according to this invention makes possible the quantitative determination of antigens and antibodies in samples or test fluids by previously preparing a calibration curve as above for the particular antigen or antibody to be determined, evaluating the rate of increase in absorbance or percent absorption per unit time in the same manner as above with a sample or test fluid containing an unknown concentration of the antigen or antibody, and comparing the thus obtained data with the calibration curve.

In this way, it is possible to determine the concentration of antigen or antibody in a test fluid with an extremely high precision by short-time measurements, as evidenced by the examples later.

In the method of our co-pending prior application (Japanese Patent Application No. 97158/76), the reaction mixture is irradiated with light having a wavelength in the range of 0.6 to 2.4 microns and longer than the average diameter of the insoluble carrier particles by a factor of at least 1.5. However, in the method according to this invention, as previously mentioned, light of any wavelength in the range of 0.6 to 2.4 microns can be used, as long as the light is so selected that, when the light is applied to the reaction mixture, an increase in absorbance or percent absorption is established. Therefore, the light is no longer restricted to that having a wavelength longer than the average diameter of the insoluble carrier particles by a factor of at least 1.5. In fact, as evidenced in Examples 9 and 8, the method according to this invention can be conducted with light of a wavelength approximately equal to the average diameter of the carrier particles (latex particles) or with light of a wavelength longer than the average diameter by a factor of about 1.1.

However, it is advantageous for the practice of this invention to use light having wavelengths in the range of 0.6 to 2.4 microns and longer than the average diameter of the insoluble carrier particles used by a factor of at least 1.1, preferably at least 1.5, since the highly precise determination of antigens and antibodies can be realized more readily by the use of light of such wavelengths.

By way of example, percent transmission spectrum in the range of 0.6 to 2.4 microns of a water layer 1 mm in thickness is shown in FIG. 1, wherein the abscissa indicates the wavelength of light and the ordinate the percent transmission of the light. It can be seen from FIG. 1 that the rays of wavelengths in the range of 0.6 to 1.4 microns are transmitted by water without substantial absorption by the water which is employed most widely as the basal media for latices and samples, and that the rays of wavelengths in the range of 1.53 to 1.88 microns are also considerably transmitted by water so that light of wavelengths in those ranges can be utilized in principle in accordance with the invention. Also, it is apparent from FIG. 1 that the rays of wavelengths in the range of 2.1 to 2.35 microns are also transmitted by water in the order of 20%, and therefore, it should be understood that the rays of such wavelengths can be used in conjunction with a highly sensitive photometer, although they are rather not preferred.

Figure 2:
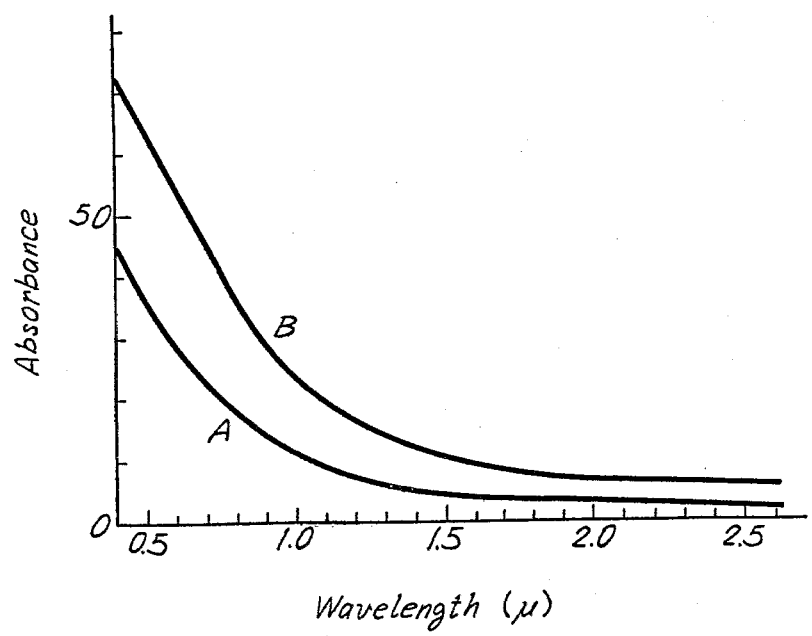
FIG. 2 is a graph which shows the change of absorbance with particle diameter of polystyrene latex.

FIG. 2 shows the relationship between the absorbance of a polystyrene latex (1% solids content by weight) in the ordinate and the wavelength of light in microns in the abscissa when a cell in 2 mm thickness is used. In FIG. 2, Curve A denotes the change in absorbance of a polystyrene latex in which the average diameter of the particles is 0.481 micron and Curve B denotes that of a polystyrene latex in which the average diameter is 0.804 micron. In the determination of absorbance, the latex was diluted for the convenience of the measurement, and the absorbance of the latex was evaluated by multiplying the actually obtained value of absorbance by the dilution factor.

As will be understood from FIG. 2, the absorbance of the latex is so significantly large with the rays of wavelengths less than 0.6 micron that it is quite difficult to measure the change in light transmittance of an antigen-antibody reaction mixture using a ray of such a wavelength, whereas with the rays of wavelengths of at least 0.8 micron, particularly at least 1 micron, the absorbance of the latex itself is relatively small so that light of wavelengths of at least 0.8 micron, preferably at least 1 micron are suitable for the above-mentioned measurement of light transmittance.

When Curve A is compared with Curve B in FIG. 2, it is recognized that the absorbance of the latex increases with increasing average diameter of the polystyrene latex particles. Accordingly it would also be understood that those latex particles having an excessively large average diameter are not useful for this invention.

In accordance with our investigation, it has been found that the insoluble carrier particles useful for this invention must have an average particle diameter of not greater than 1.6 microns and that those latex particles having an average diameter of 0.1 to 1 micron, more preferably 0.2 to 0.8 micron are preferred.

Thus, in accordance with this invention, the amount or concentration of an antigen and/or antibody in a sample can be determined by supporting the corresponding antibody and/or antigen on insoluble carrier particles (or a latex) having an average diameter within the above-defined range to prepare a sensitized latex, reacting the latex with the antigen and/or antibody in the sample, and determining the absorbance or percent absorption of the reaction mixture with light of wavelengths in the range of 0.6 to 2.4 micron, preferably 0.8 to 1.4 micron.

The insoluble carrier particles useful for this invention include those organic polymer microparticles which are substantially insoluble in the particular liquid medium used for the measurement according to the invention and which have an average diameter within the above-mentioned range, such as, for example, latices of organic polymers such as polystyrene and styrene-butadiene copolymer obtained by emulsion polymerization; dispersed coccal bacteria such as staphylococci and streptococci, Bacillus prodigiosus, rickettsia, cell membrane fragments, etc.; as well as microparticles of inorganic oxides such as silica, silica-alumina and alumina, and finely pulverized minerals, metals and the like.

In accordance with the invention, an antibody or an antigen which is reactive with the antigen and/or antibody in the sample to be measured is supported on the above-mentioned insoluble carrier particles such as, for example, latex particles (i.e., to sensitize the carrier). For this purpose, the antibody or antigen may be physically and/or chemically adsorbed on the carrier.

Antibodies consist of proteins, wherein antigens are composed of one member selected from various substances such as, for example, proteins, polypeptides, steroids, polysaccharides, lipids, pollen, dust and the like. There have already been proposed a number of methods for supporting these antibodies or antigens, particularly antibodies on insoluble carrier particles.

When an incomplete antigen, particularly a hapten is supported on insoluble carriers, it is advantageous to chemically modify the carriers with, for example, a coupling agent and subsequently bind the antigen chemically to the modified carriers. If the insoluble carrier used is a latex of a high molecular substance containing functional groups such as sulfo, amino or carboxyl or its reactive derivative group, it is also possible to chemically adsorb the antibody and/or antigen on such latex.

Of the liquid medium useful for this invention, water is the most preferable, although a mixture of water with a water-miscible organic solvent can be used. Exemplary of suitable water-miscible organic solvents are alcohols such as methanol, ethanol, etc.; ketones such as acetone; and the like.

Contrary to the known prior art methods which utilize the measurement of turbidity or the measurement of mean diffusion constant with a laser beam, the method according to this invention provides conditions that enable the insoluble carrier particles sensitized with an antibody or an antigen to react with a corresponding antigen and/or antibody as actively as possible.

On this account, in accordance with the invention, the insoluble carrier particles, for example, latex particles, which are sensitized with an antibody or an antigen (hereinafter referred to as "sensitized carrier particles") may be used as a suspension having a concentration of not less than 0.05% by weight, preferably in the range of 0.1 to 1%, more preferably 0.2 to 0.6%.

When the concentration of the sensitized carrier particles is much too high, as is apparent from FIG. 2, the transmittance of the suspension itself is so decreased that the measurement of absorbance according to the invention is made difficult. However, in the concentration range in which such a measurement of absorbance is possible, higher concentration of the sensitized carrier particles in the suspension is preferred, whereby it is possible to increase the sensitivity of the quantitative measurement of antigens and antibodies.

In accordance with the invention, also contrary to the prior art methods, the sensitized carrier particles and the antigen- and/or antibody-containing sample are reacted under non-stationary or non-standing conditions.

For this purpose, the reaction may be advantageously carried out under agitation. Since the reaction is generally carried out in a thin cell, the agitation is conveniently effected for example, by moving a rod vertically or transversely in the cell. Of course, the sensitized carrier particles and the sample may be reacted outside the cell for a certain period of time under predetermined conditions and thereafter the reaction mixture is placed in the cell for the measurement of absorbance or percent absorption. However, in order to make the reaction conditions reproducible, particularly with respect to reaction time in every measurement, the sensitized carrier particles and the sample may be reacted under predetermined, non-standing conditions directly in a cell which has been set in a spectrophotometer, whereby more accurate determination can be achieved by measuring the absorbance or percent absorption.

Thus, the present invention not only makes it possible to determine such a concentration of an antigen and/or an antibody in a sample that could heretofore be observed visually in a semiquantitative manner, but enables the determination of an antigen and/or antibody in such a trace amount that could heretofore be determined only by radioimmunoassay (RIA), with a precision equivalent to or higher than that of the RIA method.

As stated above, the present invention is characterized in that sensitized carrier particles at as high a concentration as possible may be brought into contact with and reacted with a sample.

Therefore, a cell having a thickness, for example, in the range of 0.5 to 10 mm, preferably 1 to 5 mm is suitable for use in measuring the absorbance or percent absorption of the reaction mixture.

When the method according to this invention is intended to effect a highly sensitive determination of a trace amount of an antigen or an antibody which has heretofore been subjected to the RIA method, it is particularly advantageous:

(a) to use an antigen or antibody having as high an equilibrium constant as possible, (b) to use latex particles, particularly with an average diameter of 0.2 to 0.8 micron, the size distribution of which should be as narrow as possible, and (c) to determine the absorbance or percent absorption with light of a wavelength of 0.8 to 1.4 microns.

The present invention is described in the above with respect to the determination of an antigen and/or antibody in a sample using sensitized carrier particles wherein the agglutination reaction of said particles with the antigen and/or antibody in the sample is applied to the determination (i.e., LA method).

The method according to the invention is also suitable for the determination of a sample to which the inhibitory action against the above-mentioned agglutination is applied (i.e., LI system).

Incomplete antigens such as, for example, haptens can be determined by applying the method according to the invention to the LI system.

In this case, for instance, an antigen may be supported on the insoluble carrier particles as used in this invention, the sensitized carrier particles are reacted competitively with a given amount of an antibody which has been reacted with an antigen solution of a predetermined concentration (i.e., a standard antigen solution), and the rate of increase in absorbance or percent absorption of the resulting reaction mixture per unit time is determined. The above procedure is repeated at various concentrations of the standard antigen solution to prepare a standard curve. Subsequently, an unknown sample is reacted with the same antibody of a definite concentration, and the resulting reaction mixture is then reacted with the sensitized carrier. These reactions should be carried out under substantially the same conditions as in the preparation of the standard curve. The rate of increase in absorbance or percent absorption per unit time of the final reaction mixture with the sensitized carrier particles is determined and compared with the above standard curve to determine the amount (concentration) of the antigen in the unknown sample.

Following the procedure of the above-mentioned LI system except that a certain antibody is supported on the insoluble carrier particles, an antibody in an unknown sample can be determined by the LI system. In addition, it is possible, if desired, to support both an antigen and an antibody of different species on the insoluble carrier particles and determine an antigen and an antibody in an unknown sample.

Thus, in accordance with the invention, the quantitative measurement of a wide variety of antigens and/or antibodies are possible, for example, (1) blood examination of subjects or blood donors which is indispensible for emergency operations, for example, detection of blood group substances, the Au- or HB-antigen or other contaminants in the blood, or determination of fibrin/fibrinogen degradation products (FDP) which is recently regarded as useful in the convalescent control for kidney transplantation or renal failure patients, (2) determination of human chorionic gonadotropin (hCG) which is regarded as significantly important in the pregnancy diagnosis or the convalescent control of chorioepithelioma, (3) determination of hCG, or urinary estriol glucuronide which is a metabolite of follicular hormone, said determination being required for monitoring pregnancy, (4) determination of oxytocin in blood which is considered to be a uterine contraction inducer, (5) determination of certain adrenal cortical hormones such as corticoids and aldosterone, or adrenocorticotropic hormones (ACTH), (6) determination of insulin for diabetics, or determination of follicle stimulating hormone, luteinizing hormone, estrogens, corpus luteum hormone, etc., (7) determination of gastrin or secretin which is a gastrointestinal hormone, (8) detection and determination of an antibody in the body fluid of patients with allergy, syphilis, or hemolytic streptococcicosis, rubella, autoimmune diseases such as collagen disease and other infection diseases, and the like.

The present invention may be adopted, of course, for the qualitative or semi-quantitative measurement of these antigens and/or antibodies.

In accordance with another aspect of this invention, there is provided a novel apparatus for measuring antigens and antibodies which can be used in the above-mentioned method of this invention.

The apparatus according to the invention involves (a) insoluble carrier particles for supporting an antibody or an antigen, said carrier particles having an average diameter of not greater than 1.6 microns;

(b) an adsorption cell for holding a reaction mixture obtained by reacting the antibody or antigen supported on the insoluble carrier and a corresponding antigen and/or antibody in a liquid medium, said cell having a thickness in the range of 0.5 to 10 mm;

(c) an irradiation unit for applying a light or lights of wavelengths in the range of 0.6 to 2.4 microns;

(d) means for sensing the intensity of the light of a wavelength or wavelengths in the range of 0.6 to 2.4 microns applied to the reaction mixture in the absorption cell and transmitted thereby; and (e) a means for evaluating the change of absorbance or percent absorption of the reaction mixture for the light of the wavelength sensed in step (d) as a function of the reaction time, said evaluating means being operated in response to the sensing means.

The apparatus of this invention differs from the prior art photometric apparatus in that the former possesses the structural characteristics as described in (a), (c), (d) and (e).

Figure 15:
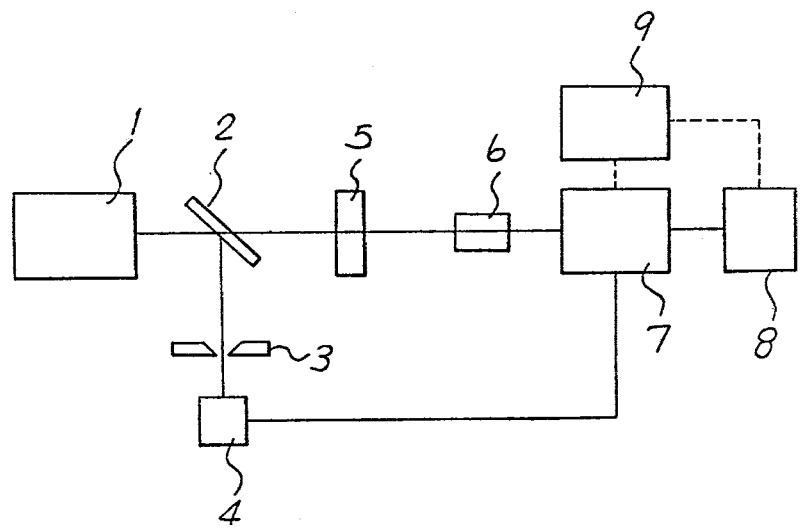
FIG. 15 is a systematic diagram which shows the basic structure of an embodiment of the apparatus according to this invention, wherein 1 indicates a monochromator; 2, a half mirror; 3, a diaphragm; 4, a compensatory detector; 5, an absorption cell; 6, a sample detector; 7, an amplifier; 8, a recorder; and 9, an integrator.

The basic structure of the apparatus according to this invention is illustrated more fully in FIG. 15 by way of example. In FIG. 15, (1) is a monochromator consisting of a light source and a filter or prism, and (2) is a semi-transparent mirror for separating the reference light, which passes through diaphragm (3) to compensatory detector (4) where the reference light is converted into an electric signal in order to detect the change in intensity of the light from the source. On the other hand, the light transmitted by half mirror (2) is applied to cell (5) containing an antigen-antibody reaction mixture and the intensity of the transmitted light is detected and converted into a electric signal by sample detector (6). The electric signal from sample detector (6) is combined with that from compensatory detector (4) and then passed to amplifier (7). The net change in percent absorption of the reaction mixture in which the change in percent absorption due to the variation of intensity of the light from the source has been compensated is recorded on recorder (8). Alternatively, the net change in percent absorption may be electrically converted into that in absorbance and recorded on recorder (8) as such.

In another way, the electric signal from amplifier (7) may, if desired, be integrated with integrator (9) for a given period of time and the integral is recorded on recorder (8).

From the change in absorbance or percent absorption with time recorded on the recorder, it is possible to obtain the rate of change (increase) in absorbance or percent absosption per unit time, whereby the antigen or antibody can be determined in accordance with this invention.

As previously mentioned, absorption cell (5) is preferably equipped with an agitator. Conventional tungsten lamp can be used as the light source to be incorporated in monochromator (1). The light emitted from this source is filtered or monochromated through a filter or prism so as to irradiate the cell with light having particular wavelengths in the range of 0.6 to 2.4 microns, preferably 0.8 to 1.4 microns. For this purpose, the filter or prism is selected from those capable of filtering or monochromating effectively the light of the above-selected wavelengths. For example, an interference filter of 1,200±50 nm can be used as the filter and a quartz or glass prism as the prism.

Also as previously mentioned, a light emitting diode such as, for example, a gallium arsenide-type light emitting diode with a half width of 0.05 micron and with a peak emission wavelength of 0.94 micron, or the like may be used as another light source.

Sample cell (5) may be composed of transparent glass or synthetic resin (e.g., an acrylic resin) and may be a box-shape having a rectangular cross section. The cell thickness may be in the range of 0.5 to 10 mm, preferably 1 to 5 mm. Advantageously, the transmissive windows of the cell have at least 30% transmission, preferably more than 80% transmission, for the light of wavelengths of 0.6 to 2.4 microns. As detectors (4) and (6), any type capable of transducing an intensity of received light into an electric signal of strength proportional to the intensity of the light can be used. For example, lead sulfide photoconductive element or silicon photodiode may be used to advantage.

The electric signals transduced with the detectors may be amplified with amplifier (7) in the conventional way and recorded on recorder (8).

Having generally described this invention, a more complete understanding can be obtained by reference to certain examples which are provided herein for purpose of illustration only and are not intended to be limiting in any manner.

EXAMPLE 1

(1) Preparation of an antifibrinogen antibody-sensitized latex (anti-Fg-latex) reagent To 10 ml of a glycine buffer solution of anti-(human fibrinogen) (Fg) antibody (2 mg/ml concentration), 0.5 ml of a polystyrene latex with an average particle diameter of 0.091 micron (Dow Chemical Co., 10% solids content by weight) and 0.5 ml of another polystyrene latex with an average particle diameter of 0.220 micron (ditto) were added, and the mixture was stirred at room temperature for 30 minutes, then warmed to 40° C. and stirred for an additional 30 minutes at this temperature, and centrifuged (at 12,000 rpm) for 50 minutes with cooling at 2° to 4° C. The precipitate was separated by decantation and the collected anti-(Fg) antibody-sensitized (supported) latex particles were suspended in a bovine serum albumin solution (0.2 wt. % concentration) to prepare an anti-Fg-sensitized latex reagent containing the sensitized latex particles at a concentration of 1% by weight.

(2) Preparation of a calibration curve

To a 0.1 ml of the anti-Fg-latex reagent as prepared in Part (1) above which was placed in a small test tube, 0.1 ml of a glycine buffer solution (pH 9.6) and subsequently 0.2 ml of a standard Fg solution at a concentration indicated in Table-A below which was dissolved in an isotonic sodium chloride solution containing 0.2% by weight of bovine serum albumin were added and thoroughly mixed by shaking for 5 seconds at room temperature. Thereafter the mixture was immediately transferred to an acrylic resin cell having a thickness of 2 mm equipped with an L-shaped stirring rod movable up and down, and the change of absorbance of the reaction mixture with time was recorded while the reaction mixture was stirred at 160 strokes per minute. The absorbance was determined with a Hitachi 340 spectrophotometer with the measuring wavelength being set at 950 nm and the photometric mode to "Absorbance". The light of the measuring wavelength had a slit width of about 3 nm.

The thus obtained chart for the change of absorbance with time recorded on the spectrophotometer is shown in FIG. 3, wherein Curves A, B, C and D correspond to Fg concentrations of 0.0156, 0.0313, 0.0625 and 0.125 μg/ml, respectively. On this chart, a straight line was then drawn along the approximately straight portion of each curve in an early stage as possible after the start of the recording, and the slope of the straight line was calculated. The thus obtained values are given in the column of "rate" in Table-A below, in which the rate of change in absorbance is expressed in absorbance/min. The straight lines drawn in the above-mentioned manner are illustrated in FIG. 3 as A', B', C' and D'. The correlation between the concentration of antigen and the thus obtained rate of increase in absorbance due to the agglutination of the latex was exhibited graphically, whereby the calibration curve shown in FIG. 4 was prepared.

Table - A

| Concentration of standard Fg solution (μg/ml) | Rate of absorbance increase at 950 nm (absorbance/min.) |
|---|---|
| 0.0156 | 0.0008 |
| 0.0313 | 0.00264 |
| 0.0625 | 0.00480 |
| 0.125 | 0.0103 |
| 0.250 | 0.0256 |
| 0.500 | 0.0566 |
| 1.00 | 0.152 |
| 2.00 | 0.300 |
| 4.00 | 0.514 |

(3) Assay of Fg in unknown samples

A sample of blood or urine was collected from a subject and, if the sample was blood, the serum was separated therefrom in the conventional manner. A 0.2 ml aliquot of the undiluted or diluted sample (with dilution factor as indicated in Table B) was mixed with 0.1 ml of the anti-Fg-latex reagent as prepared in Part (1) and 0.1 ml of a glycine buffer solution (pH 9.6) in exactly the same manner as described in Part (2), and the rate of increase in absorbance was evaluated in the same manner as described in Part (2). On the calibration curve obtained in Part (2), the Fg concentration corresponding to the thus obtained value of the rate of increase in absorbance was read. The results are summarized in Table-B below.

For the purpose of comparison, Table-B also involves the data obtained in accordance with the two conventional methods, that is, the radioimmunoassay (RIA) method (S. M. Ratky, et al., Brit. J. Haematol. 30, 145-149, 1975) and the slide method (Fujimaki, Tamura and Takashashi, Rinsho Kagaku (Clinical Science), 12, 507, 1976, Japan; and Fujimaki, Ikematsu, Takeuchi and Kato, Rinsho Byori (Japanese Journal of Clinical Pathology), 21, 973, 1973).

Table - B

| Subject No. | Unknown sample Material | Unknown sample Dilution factor | Rate of increase in absorbance (Absorbance/min. × 10²) | Fg concentration in unknown sample (μg/ml) Method of this invention | Fg concentration in unknown sample (μg/ml) RIA method | Fg concentration in unknown sample (μg/ml) Slide method |
|---|---|---|---|---|---|---|
| 1 | Urine | × 16 | 3.7 | 5.28 | 4.892 | 8.0 |
| 2 | " | × 1 | 3.25 | 0.30 | 0.282 | 0.5 |
| 3 | " | " | 0.087 | 0.015 | 0.020 | <0.5 |
| 4 | " | " | <0.05 | <0.01 | 0.006 | " |
| 5 | " | " | 0.365 | 0.049 | 0.052 | " |
| 6 | " | " | 0.088 | 0.015 | 0.011 | " |
| 7 | " | " | 0.330 | 0.045 | 0.023 | " |
| 8 | " | " | <0.05 | <0.01 | 0.006 | " |
| 9 | " | " | 0.332 | 0.045 | 0.072 | " |
| 10 | Serum | × 10 | 0.671 | 0.810 | 0.789 | 1.0 |
| 11 | " | " | 0.665 | 0.805 | 0.850 | 1.0 |
| 12 | " | " | 1.32 | 1.42 | 1.335 | 1.25 |
| 13 | " | " | 0.698 | 0.84 | 0.870 | 1.0 |

EXAMPLE 2

(1) Preparation of an anti-(hCG) antibody-sensitized latex (anti-hCG-latex) reagent An anti-hCG-sensitized latex reagent was prepared in the same manner as described in Part (1) of Example 1, except that anti-(human chorionic gonadotropin) antibody (anti-hCG) was used in place of the anti-(human fibrinogen) antibody, a monodispersed polystyrene latex having an average particle diameter of 0.220 micron was used instead of the equi-volume mixture of the two polystyrene latices of 0.091 and 0.220 micron in average diameter and that the concentration of latex particles in the final reagent was 0.25%.

(2) Preparation of calibration curve

In a small test tube, 0.15 ml of the anti-hCG-latex reagent prepared in Part (1) above and 0.15 ml of a standard hCG solution dissolved at the concentration indicated in Table-C below in an isotonic sodium chloride solution containing 0.2% by weight of bovine serum albumin were thoroughly mixed by shaking for 5 seconds. Immediately thereafter the mixture was transferred to an acrylic resin cell of 4 mm in thickness equipped with a compact agitator having a rotary blade of 2.4 mm in diameter, and the change of percent absorption of the reaction mixture with time was recorded while the mixture was stirred at 1,200 rpm. The determination of percent absorption was conducted with a Ga-As light emitting diode (Monsanto Co., Mode ME-7124, a peak emission wavelength: 940 nm, half width: 50 nm) as the source. The light emitted from the source was directly applied to the cell and the transmitted light was measured with a silicon photocell (Hamamatsu TV, Model S 874-8K). After the output of the photocell was amplified, the change of percent absorption with time was recorded on a pen-recorder. The thus obtained chart is shown in FIG. 5 (a). On this chart, a straight line was then drawn along the approximately straight portion of each curve in as early stage as possible after the start of the recording, and the slope of the straight line was circulated. The thus obtained values are given in the column of "rate" in Table-C below, in which the rate of change in percent absorption is expressed in %/min. This experiment was repeated twice for each concentration in order to check the reproducibility of the results. From the data of Table-C, a calibration curve shown in FIG. 6 (a) was prepared by exhibiting graphically the correlation between the concentration of antigen and the rate of increase in percent absorption due to the agglutination of the latex. FIG. 6 (a) is plotted on a log scale in both axes.

Table - C

| Concentration of standard hCG solution (IU/ml) | Rate of change in percent absorption at 940 nm (%/min.) First | Rate of change in percent absorption at 940 nm (%/min.) Second | Rate of change in percent absorption at 940 nm (%/min.) Mean |
|---|---|---|---|
| 0.078 | 1.84 | 1.78 | 1.81 |
| 0.156 | 3.12 | 3.18 | 3.15 |
| 0.312 | 5.50 | 5.50 | 5.50 |
| 0.625 | 9.62 | 9.40 | 9.51 |
| 1.25 | 14.9 | 14.8 | 14.85 |

FIG. 5 (b) shows the chart obtained by converting the data of FIG. 5 (a) which was actually recorded on a recording paper into the corresponding change of absorbance. Also on the chart of FIG. 5 (b), the rate of change in absorbance was determined in the same manner as above using the approximately straight portion of each absorbance curve in as early stage as possible after the start of the reaction. FIG. 6 (b) is a graph showing the relationship between the thus determined rate of change in absorbance and the concentration of standard hCG solution. The assay of unknown samples described in Part (3) below also could be effected from FIG. 6 (b).

(3) Assay of hCG in unknown samples

A sample of blood or urine was collected from a subject and if the sample was blood, the serum was isolated therefrom in the conventional manner. The sample was then diluted as indicated in Table-D below. In exactly the same way as described in the preceding Part (2), 0.15 ml of the dilute sample was reacted with 0.15 ml of the anti-hCG-latex reagent prepared in Part (1) above and the change of percent absorption with time was recorded to determine the rate of increase in percent absorption. The thus obtained value was compared with the calibration curve and the concentration of hCG corresponding to this value of the rate of increase in percent absorption was read from the curve. The results are summarized in Table-D below. For comparison, Table-D includes the data obtained with the same sample in accordance with the RIA method (Radioimmunoassay Method, K. Okumura, J. of Jap. Endocrinologic Soc., 52, 105, 1976).

Table - D:

| | | Assay of unknown sample | | | | hCG concentration in unknown sample (IU/ml) | |
|---|---|---|---|---|---|---|---|
| Sample No. | Type of sample | Patient's name (Sex) | Diagnosis | Dilution factor | Rate (%/min.) | Method of this invention | RIA method |
| 1 | Urine | H. M. (F) | Pregnancy (10th week) | × 100 | 9.2 | 60 | 65.16 |
| 2 | " | K. O. (F) | Hydatid mole (8th week) | × 1000 | 10.2 | 690 | 682.9 |
| 3 | " | R. H. (F) | After removal of hydatid mole | × 1 | 7.8 | 0.45 | 0.484 |
| 4 | " | G. M. (M) | Right testiculoma | × 1 | 3.8 | 0.20 | 0.182 |
| 5 | " | T. I. (F) | Partial abortion (4th week) | × 1 | 3.5 | 0.18 | 0.194 |
| 6 | Serum | T. Y. (F) | Hydatid mole | × 1 | 1.7 | 0.075 | 0.0741 |
| 7 | " | E. S. (M) | Testiculoma | × 10 | 9.6 | 6.4 | 6.17 |
| 8 | " | S. K. (F) | Hydatid mole | × 1 | 7.7 | 0.48 | 0.544 |
| 9 | " | H. N. (M) | Malignant thymoma | × 1 | 10.0 | 0.69 | 0.673 |
| 10 | " | R. W. (F) | Pregnancy (6th week) | × 100 | 13.2 | 95 | 100.3 |

EXAMPLE 3

Figure 7:
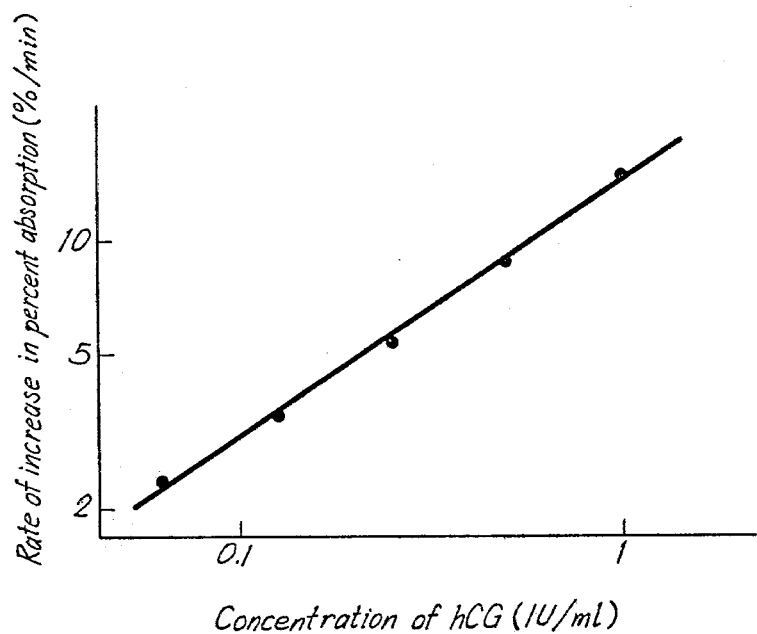
FIG. 7 is a chart which shows the relationship between the concentration of hCG and the rate of increase in percent absorption at 950 nm evaluated from the reaction of an anti-hCG-sensitized latex reagent having an average diameter of 0.220 micron with each of standard hCG solutions of various concentration.

A 0.1 ml aliquot of an anti-(hCG) antibody-sensitized latex reagent with 0.33% latex content prepared in the same manner as described in Part (1) of Example 2 was reacted with 0.1 ml of a standard hCG solution in exactly the same manner as described in Part (2) of Example 2 and the change of percent absorption with time was recorded. The determination of percent absorption was carried out with the same assembly as in Example 2, except that the irradiation light was a monochromatic light with a wavelength of 950 nm and a slit width of 30 nm (corresponding to a mechanical slit width of 0.36 mm) which was emitted from a prism spectrophotometer (Hitachi Model EPU-2) used as the light source and that the cell had a thickness of 3 mm. From a straight portion of the chart on the pen recorder which indicated the change of percent absorption with time, the rate of change in percent absorption per unit time was evaluated and plotted on log-log graph paper as ordinate against the concentration of standard hCG solution as abscissa, thereby the calibration curve shown in FIG. 7 being obtained. Using this calibration curve, hCG concentrations of unknown samples could be determined.

EXAMPLE 4

An anti-Fg-latex reagent with 0.50% latex content was prepared following the same procedure described in Part (1) of Example 1, except that the equi-volume mixture of the polystyrene latex of 0.091 micron in average diameter and that of 0.220 micron was replaced by a monodispersed polystyrene latex of 0.312 micron in average diameter (Dow Chemical).

Figure 8:
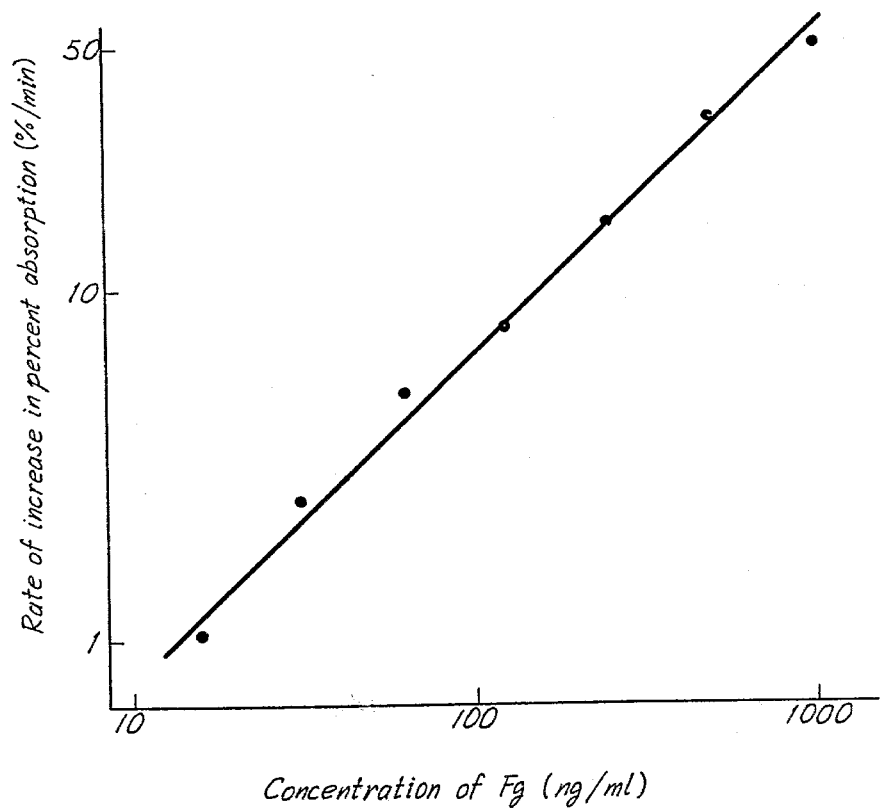
FIG. 8 is a chart which shows the relationship between the concentration of Fg and the rate of increase in percent absorption at 950 nm evaluated from the reaction of an anti-Fg-sensitized latex reagent having an average diameter of 0.312 micron with each of standard Fg solutions of various concentrations.

In a small test tube, 0.2 ml of the latex reagent and 0.2 ml of a standard Fg solution as described in Example 1 were mixed by shaking for 5 seconds. Immediately thereafter the reaction mixture was transferred to a cell having a thickness of 2 mm and the change in percent absorption with time was recorded while the mixture was agitated with a stirring rod moving up and down as in Example 1. The determination of percent absorption was conducted in the same way as described in Example 3 except for stirring means. The data thus obtained was then processed in exactly the same way as in Example 3, resulting in the correlation data between the concentration of standard Fg solution and the rate of change in percent absorption as given in Table-E, from which a calibration curve as shown in FIG. 8 was prepared. Using this calibration curve, the amounts of Fe in unknown samples could be determined.

Table - E

| Concentration of standard Fg solution (μg/ml) | Rate of increase in percent absorption (%/min.) |
|---|---|
| 15.6 | 1.03 |
| 31.3 | 2.48 |
| 62.5 | 4.95 |
| 125 | 7.70 |
| 250 | 15.15 |
| 500 | 30.0 |
| 1,000 | 48.5 |

EXAMPLE 5

Figure 9:
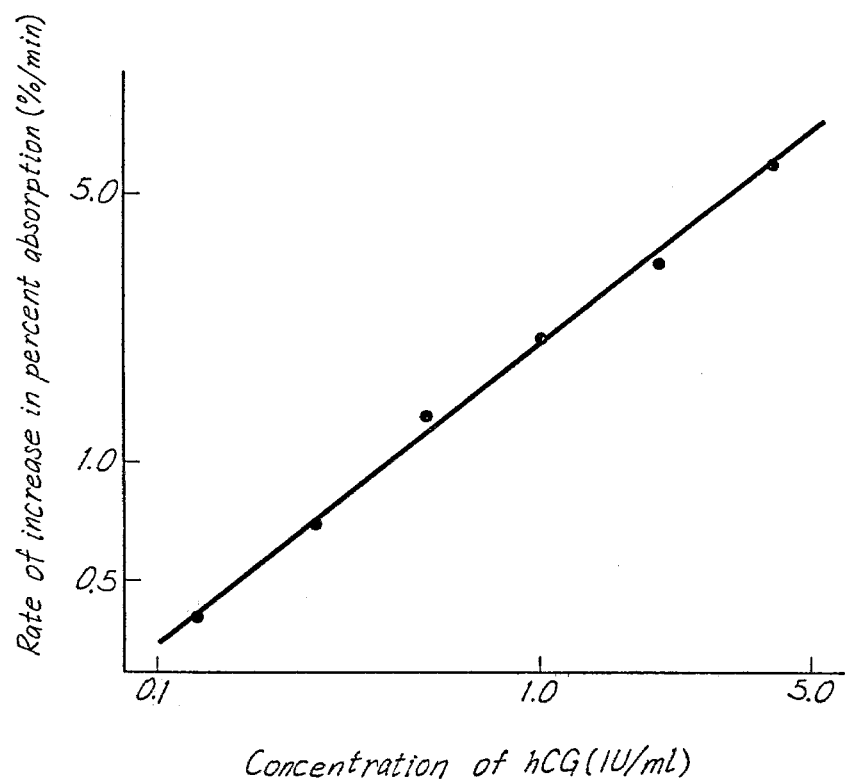
FIG. 9 is a chart which shows the relationship between the concentration of hCG and the rate of increase in percent absorption for polychromatic light of wavelengths of 800 to 1,100 nm evaluated from the reaction of an anti-hCG-sensitized latex reagent having an average diameter of 0.220 micron and each of standard hCG solutions of various concentrations.

Using the same anti-hCG-latex reagent as used in Example 3, the rate of change in percent absorption was evaluated. The assembly used for the measurement was also the same as used in Example 3, except that the light source component was replaced by a combination of a conventional tungsten lamp (12 V, 8 W) and an optical filter (Ditric Optics, D 800) and that the cell was irradiated with light containing no spectral component of wavelength shorter than 800 nm. The data thus obtained was processed in exactly the same manner as in Example 3, thereby the results of Table-F below which indicates the correlation between the hCG concentration and the rate of increase in percent absorption being obtained. The results were then exhibited graphically to obtain the calibration curve shown in FIG. 9, with which the amounts of hCG in unknown samples could be determined in the same way as in Example 2.

Table - F

| Concentration of standard hCG solution (IU/ml) | Rate of change in percent absorption (%/min.) |
|---|---|
| 0.125 | 0.40 |
| 0.25 | 0.70 |
| 0.5 | 1.3 |
| 1.0 | 2.1 |
| 2.0 | 3.3 |
| 4.0 | 6.0 |

EXAMPLE 6

An anti-(hCG) antibody-sensitized latex reagent prepared in exactly the same manner as in Example 2 was reacted with each standard hCG solution having the concentration indicated in Table-G below. The change of percent absorption was recorded using the light source and the detector identical to that used in Example 2 except that an integrator was connected between the detector and the recorder. The integration was started coincidentally with the stirring and an integration of percent absorption for the period of 9 seconds was repeated with a pause of one second therebetween. The rate of change was evaluated from the integrals of the fifth and seventh 9-seconds' period. The results are summarized in Table-G below.

Table - G

| Concentration of standard hCG solution (IU/ml) | Integral (a) of 5th 9-seconds' period (reading on graph) | Integral (b) of 7th 9-seconds' period (reading on graph) | (b) − (a) |
|---|---|---|---|
| 0.0625 | 0.5 | 1.5 | 1.0 |
| 0.125 | 14.5 | 16.5 | 2.0 |
| 0.25 | 22.5 | 27.0 | 4.5 |
| 0.50 | 39 | 47 | 8.0 |
| 1.0 | 70 | 90 | 20 |
| 2.0 | 96 | 141 | 45 |

Figure 10:
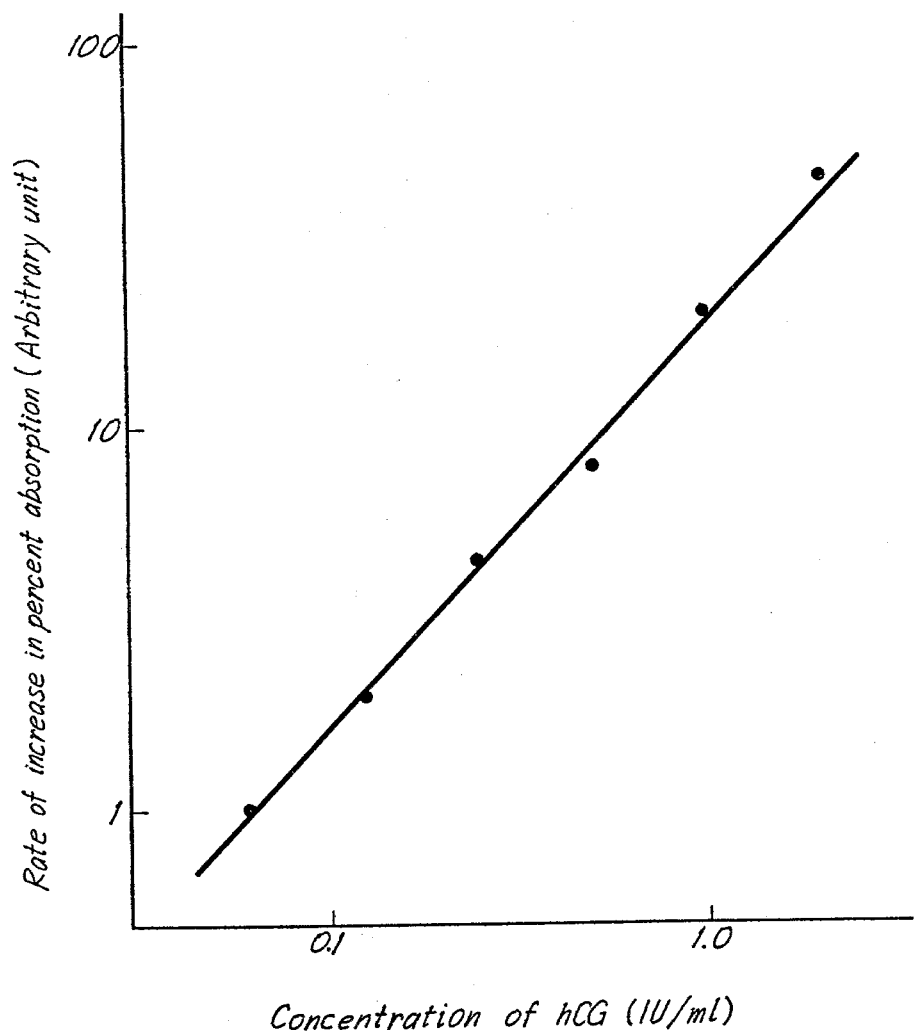
FIG. 10 is a chart which shows the relationship between the concentration of hCG and the rate of increase in percent absorption for light having a peak emission wavelength of 940 nm evaluated with an integrator from the reaction of an anti-hCG-sensitized latex reagent having an average diameter of 0.220 micron and each of standard hCG solutions of various concentrations.

The above data is graphically exhibited in FIG. 10. Using the graph of FIG. 10 as a standard curve, the concentration of hCG in unknown samples could be determined in the same way as above.

EXAMPLE 7

An anti-hCG-sensitized latex reagent was prepared in the same way as described in Part (1) of Example 2, except that the concentration of the latex particles with an average diameter of 0.220 micron in the final sensitized latex reagent was adjusted to 1.0% by weight.

Figure 11:
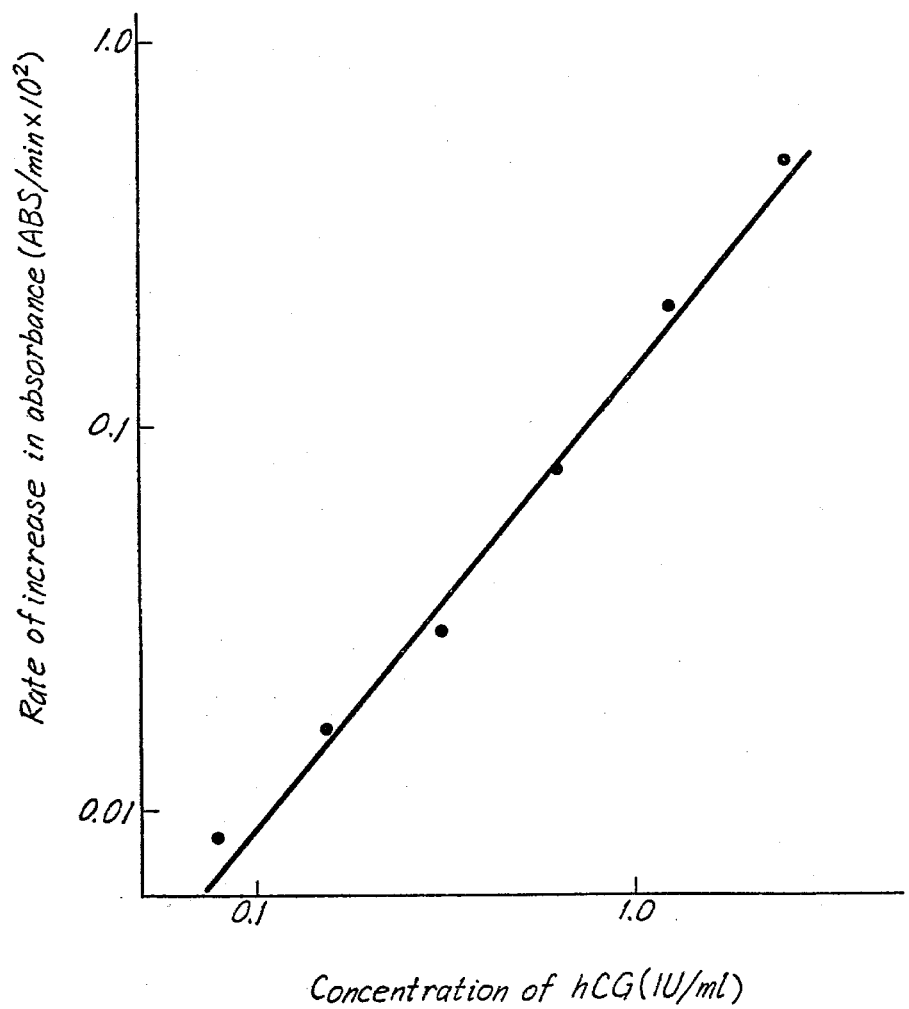
FIG. 11 is a chart which shows the relationship between the concentration of hCG and the rate of increase in absorbance at 950 nm evaluated from the reaction of an anti-hCG-sensitized latex reagent having an average diameter of 0.220 micron and each of standard hCG solutions of various concentrations.

The subsequent reaction and measurement were carried out using the same procedure and the same apparatus as in Part (2) of Example 1, except that the standard Fg solutions were replaced by the standard hCG solutions of various concentrations indicated in Table-H below. From the data thus obtained was prepared a calibration curve as shown in FIG. 11 which indicates the relationship between the concentration of antigen and the rate of increase in absorbance. Using this calibration curve, the concentration of hCG in unknown samples could be determined in the same way as in Example 2.

Table - H

| Concentration of standard hCG solution (IU/ml) | Rate of increase in absorbance at 950 nm (absorbance/min. × $10^2$) |
|---|---|
| 0.078 | 0.0086 |
| 0.156 | 0.016 |
| 0.313 | 0.0278 |
| 0.625 | 0.075 |
| 1.25 | 0.197 |
| 2.5 | 0.480 |

EXAMPLE 8

An anti-Fg-sensitized latex reagent (content of latex particles: 1% by weight) was prepared in the same way as described in Part (1) of Example 1, except for the use of a polystyrene latex having an average diameter of 0.804 micron (Dow Chemical, 10 wt. % solids content).

Figure 12:
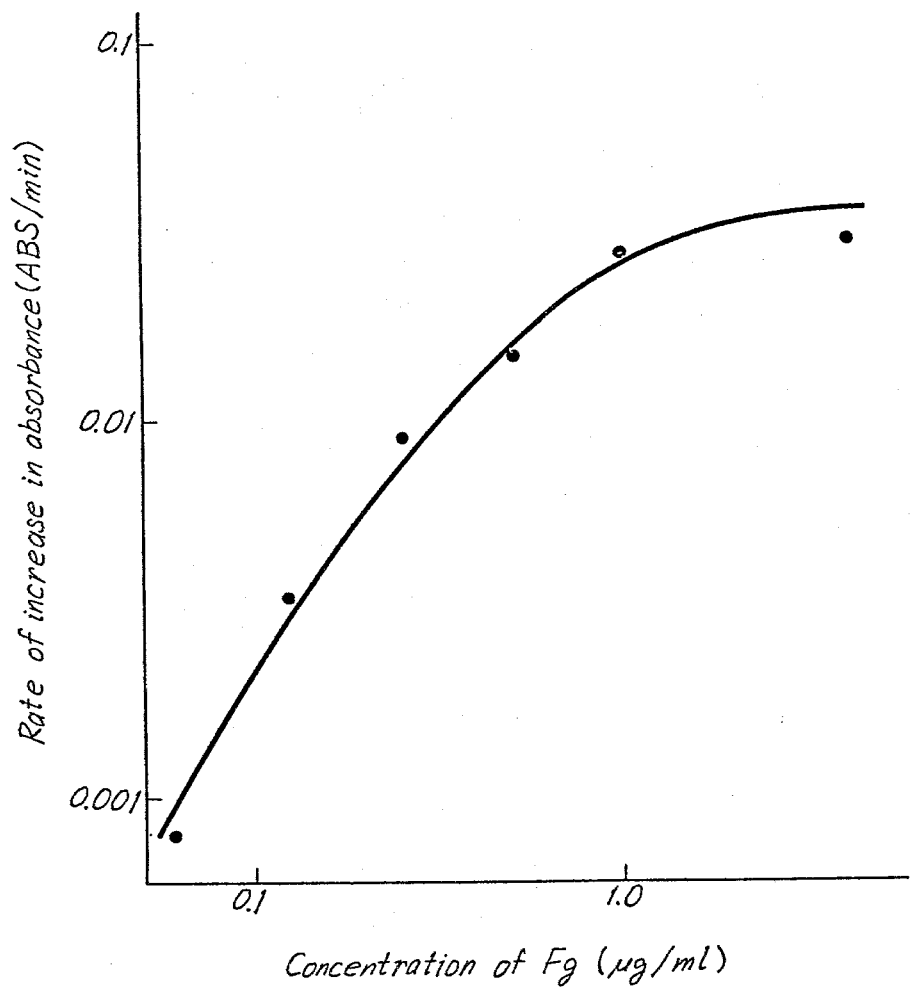
FIG. 12 is a chart which shows the relationship between the concentration of Fg and the rate of increase in absorbance at 900 nm evaluated from the reaction of an anti-Fg-sensitized latex reagent having an average diameter of 0.804 micron and each of standard Fg solutions of various concentrations.

In a small test tube, 0.1 ml of the thus obtained anti-Fg-latex reagent, 0.1 ml of a glycine buffer solution (pH 9.6) and 0.2 ml of one of standard Fg solutions containing Fg at various concentrations indicated in Table-I below in a medium of isotonic sodium chloride solution containing 0.1% by weight of bovine serum albumin, were mixed by shaking for 5 seconds. Thereafter the change in absorbance with time was measured with the apparatus identical to that used in Part (2) of Example 1 at a wavelength of 900 nm (slit width: about 3 nm). The rate of increase in absorbance due to the agglutination of the latex was evaluated in the same manner as described in Part (2) of Example 1 (as shown in Table-I below), and the correlation thereof to the antigen concentration of standard solution was exhibited graphically, thereby the calibration curve shown in FIG. 12 being obtained.

It can be seen from these data that, even if the wavelength at which the absorbance is measured is longer than the average particle diameter of a latex by a factor as low as 1.13, a sufficient correlation to determine the concentration of an antigen is established at concentrations of the antigen in standard solutions of not more than 1 µg/ml.

Table - I

| Concentration of standard Fg solution (µg/ml) | Rate of increase in absorbance at 900 nm (absorbance/min.) |
|---|---|
| 0.0625 | 0.0008 |
| 0.125 | 0.0034 |
| 0.250 | 0.0090 |
| 0.500 | 0.0148 |
| 1.00 | 0.0276 |
| 4.00 | 0.0296 |

EXAMPLE 9

A anti-hCG-latex reagent containing 0.3% by weight of latex particles was prepared in the same manner as in Example 2, except that the polystyrene latex having an average particle diameter of 0.220 micron was replaced by that having an average diameter of 1.091 microns (Dow Chemical, 10 wt. % solids content).

A 0.2 ml aliquot of the thus prepared anti-hCG-latex reagent was placed in a small test tube and a 0.2 ml of a standard hCG solution of a concentration indicated in Table-J below in a medium of isotonic sodium chloride solution containing 0.1 wt. % bovine serum albumin was added. Thereafter the change in absorbance of the reaction mixture with time was recorded using the same procedure and the same apparatus as in Part (2) of Example 1, except for setting the wavelength at 1,100 nm (slit width: about 3 nm) in place of 950 nm. On the basis of this record of the change in absorbance with time, the calibration curve shown in FIG. 13 was obtained according to the same procedure as in Part (2) of Example 1.

Figure 13:
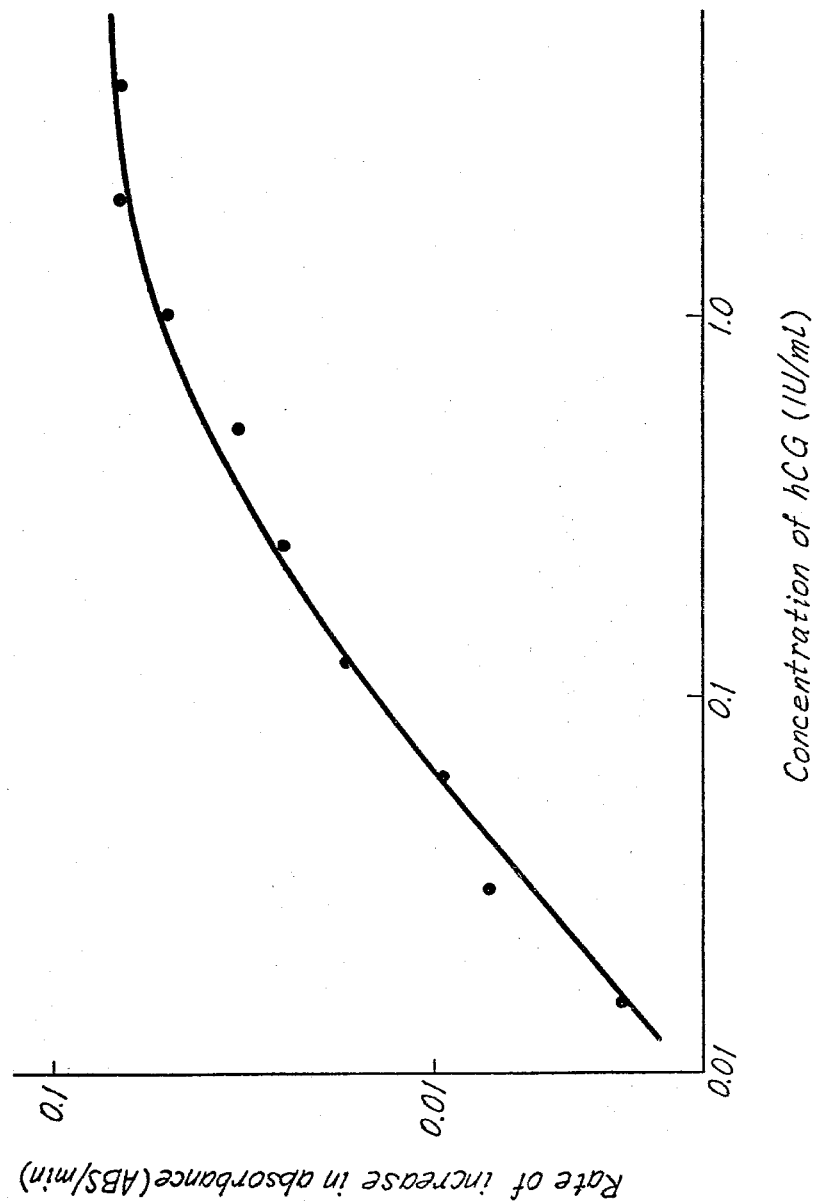
FIG. 13 is a chart which shows the relationship between the concentration of hCG and the rate of increase in absorbance at 1,100 nm evaluated from the reaction of an anti-hCG-sensitized latex reagent having an average diameter of 1.09 microns and each of standard hCG solutions of various concentrations.

It can be seen from FIG. 13 that, even if the ratio of wavelength to average diameter of latex is nearly 1.0, the method according to this invention is practical at hCG concentrations of not more than 1.0 IU/ml.

Table - J

| Concentration of standard hCG solution (IU/ml) | Rate of increase in absorbance at 1,100 nm (absorbance/min.) |
|---|---|
| 0.0156 | 0.0032 |
| 0.0313 | 0.0072 |
| 0.0625 | 0.0095 |
| 0.125 | 0.0169 |
| 0.250 | 0.025 |
| 0.500 | 0.033 |
| 1.00 | 0.050 |
| 2.00 | 0.066 |
| 4.00 | 0.066 |

EXAMPLE 10

Figure 14:
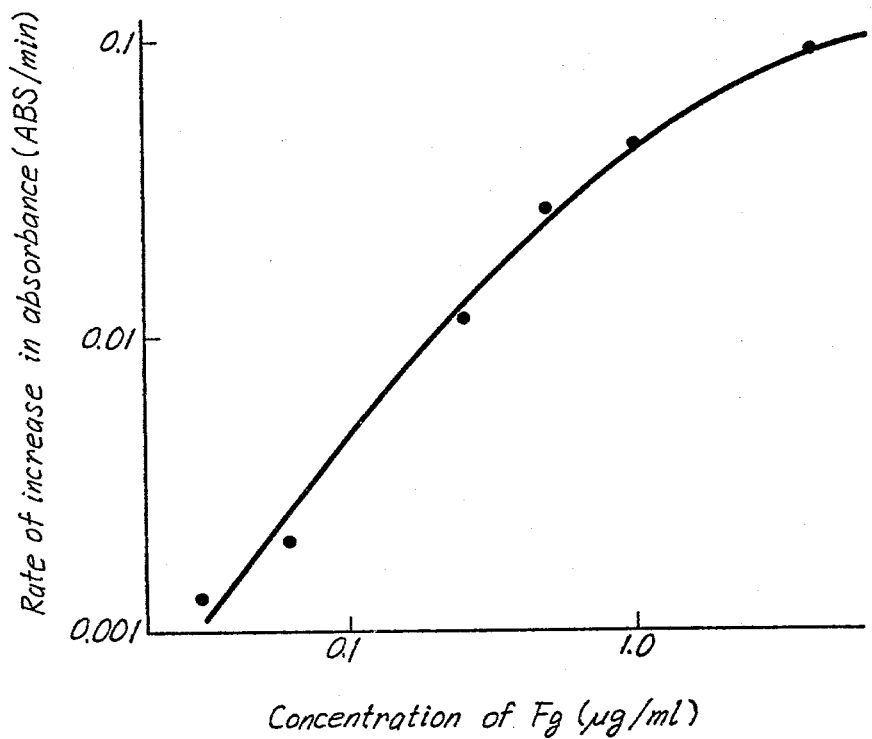
FIG. 14 is a chart which shows the relationship between the concentration of Fg and the rate of increase in absorbance at 1,650 nm evaluated from the reaction of an anti-Fg-sensitized latex reagent having an average diameter of 0.804 micron and each of standard Fg solutions of various concentrations.

Following the procedure of Example 8, a series of experiments were conducted using an anti-Fg-sensitized latex (average diameter: 0.804 micron) identical to that used in Example 8 and standard Fg solutions of various concentrations indicated in Table-K below in a medium of isotonic sodium chloride solution containing 0.1 wt. % bovine serum albumin. The measurements of absorbance were taken at a wavelength of 1,650 nm, instead of 900 nm, with slit width of about 3 nm. The thus obtained calibration curve is sufficient to determine the concentration of the antigen, as shown in FIG. 14.

Table - K

| Concentration of standard Fg solution (μg/ml) | Rate of increase in absorbance at 1,650 nm (absorbance/min.) |
|---|---|
| 0.0313 | 0.00128 |
| 0.0625 | 0.0020 |
| 0.250 | 0.0116 |
| 0.500 | 0.027 |
| 1.00 | 0.044 |
| 4.00 | 0.092 |

Having now fully described the invention, it will be apparent to one of ordinary skill in the art that many changes and modifications can be made thereto without departing from the spirit or scope of the invention as set forth herein.

What is claimed as new and intended to be covered by Letters Patent is:

1. An absorbance method of measuring antigens and antibodies comprising reacting an antigen or antibody or a mixture thereof in a liquid medium with the corresponding antibody, antigen or mixture thereof which has been supported on insoluble carrier particles having an average diameter of not greater than 1.6 microns to sensitize the carrier particles, and wherein said carrier particles are present in the reaction mixture at a concentration of 0.05 to 1% by weight, irradiating the reaction mixture with light having a wavelength or wavelengths in the range of 0.6 to 2.4 microns to measure the transmitted light at 2 or more points of time as the reaction proceeds, and then evaluating an increase in absorbance or percent absorption of the reaction mixture for a given period of time.

2. The method according to claim 1 wherein an antigen or antibody to be determined is reacted with the corresponding antibody or antigen supported on the insoluble carrier particles in the liquid medium under predetermined, substantially fixed conditions, and the rate of increase in absorbance or percent absorption of the reaction mixture per unit time is evaluated at about a fixed time after the reaction has been started.

3. The method according to claim 1 wherein an antigen or antibody to be determined is reacted with the corresponding antibody or antigen supported on the insoluble carrier particles in the liquid medium under predetermined, substantially fixed conditions, and thereafter the rate of increase in absorbance or percent absorption of the reaction mixture per unit time is evaluated in such stage that the reaction proceeds steadily.

4. The method according to claim 3 wherein said rate of increase is evaluated at an early time after the reaction has come to the steady state.

5. The method according to claim 1 wherein an antigen or antibody in a test fluid is reacted with the corresponding antibody or antigen supported on the insoluble carrier particles under predetermined, substantially fixed conditions and thereafter the rate of increase in absorbance or percent absorption of the reaction mixture per unit time is evaluated in such stage that said absorbance or percent absorption increases steadily by the lapse of time.

6. The method according to claim 1 wherein an antigen or antibody in a test fluid is reacted with the corresponding antibody or antigen supported on the insoluble carrier particles under predetermined, substantially fixed conditions and the rate of increase in absorbance or percent absorption of the reaction mixture per unit time is evaluated in such stage that said absorbance or percent absorption increases steadily for the first time after the reaction has been started.

7. The method according to any one of claims 1 to 6 wherein an antigen or antibody in a test fluid is reacted with the corresponding antibody or antigen supported on the insoluble carrier particles under predetermined, substantially fixed conditions, the absorbance or percent absorption of the reaction mixture is measured and stored at two or more points of time after the reaction has been started, and the stored data is used to evaluate the rate of increase in absorbance or percent absorption of the reaction mixture per unit time.

8. The method according to claim 1 wherein the insoluble carrier particles have an average diameter in the range of 0.1 to 1.0 micron.

9. The method according to claim 1 wherein the insoluble carrier particles have an average diameter in the range of 0.2 to 0.8 micron.

10. The method according to claim 1 wherein the carrier particles consist essentially of fine powder of an organic high molecular substance or inorganic substance which is substantially insoluble in the liquid medium.

11. The method according to claim 10 wherein said fine powder of the organic high molecular substance is fine powder of synthetic resin or bacteria or cell membrane fragments.

12. The method according to claim 10 wherein said fine powder of the organic high molecular substance is particles of a polystyrene latex.

13. The method according to claim 10 wherein said fine powder of the inorganic substance consists of at least one member selected from the group consisting of metals, inorganic oxides or minerals.

14. The method according to claim 10 wherein said fine power of the inorganic substance consists of silica, alumina or silica-alumina.

15. The method according to claim 1 wherein the reaction of said antigen or antibody or a mixture thereof with said corresponding antibody- and/or antigen-sensitized insoluble carrier particles is carried out under such conditions as to accelerate contact of the carrier particles with one another as much as possible.

16. The method according to claim 1 wherein the reaction of said antigen or antibody or a mixture thereof with said corresponding antibody- and/or antigen-sensitized insoluble carrier particles is carried out under predetermined, substantially fixed conditions which accelerate contact of the carrier particles with one another while the absorbance or percent absorption of the reaction mixture is measured.

17. The method according to claim 15 or 16 wherein said reaction is carried out with agitation.

18. The method according to claim 1 wherein the reaction mixture is irradiated with monochromatic or polychromatic light having a wavelength or wavelengths in the range of 0.6 to 2.4 microns.

19. The method according to claim 1 wherein the reaction mixture is irradiated with monochromatic or polychromatic light having a wavelength or wavelengths in the range of 0.8 to 1.4 microns.

20. The method according to claim 1 wherein the light has a wavelength or wavelengths which are longer than the average diameter of the carrier particles by a factor of at least 1.1 and at which the absorbance or percent absorption of the reaction mixture increases as the reaction proceeds.

21. The method according to claim 1 wherein the light has a wavelength or wavelengths which are longer than the average diameter of the carrier particles by a factor of at least 1.5 and at which the absorbance or percent absorption of the reaction mixture increases as the reaction proceeds.

22. The method according to claim 1 wherein the carrier particles are present in the reaction mixture at a concentration in the range of 0.1% to 0.6% by weight.

23. The method according to claim 1 wherein the liquid medium is water or a mixture of water and a water-miscible organic solvent.

24. The method according to claim 1 wherein a test fluid which may be diluted or concentrated and which contains an antigen or antibody is reacted with a suspension of the carrier particles on which the corresponding antibody or antigen has been supported.

25. The method according to claim 1 wherein a test fluid containing an antibody or antigen to be determined is first reacted with the corresponding antigen or antibody and the resulting reaction mixture is then reacted with a suspension of the carrier particles on which the corresponding antibody or antigen has been supported.

26. The method according to claim 1 wherein an antibody or antigen is supported on the insoluble carrier particles by physical and/or chemical adsorption thereon.

27. The method according to claim 1 wherein an antibody or antigen is supported on the insoluble carrier particles by chemical bonding through a coupling agent.

28. An apparatus for determining antigens and antibodies, which involves:
   (a) insoluble carrier particles for supporting an antibody or antigen which corresponds to an antigen or antibody to be determined, said carrier particles having an average diameter of not greater than 1.6 microns;
   (b) an absorption cell for holding the reaction mixture of an antibody or antigen supported on the insoluble carrier and an antigen or antibody or a mixture thereof to be determined in a liquid medium, said cell having a thickness of 0.5 to 10 mm;
   (c) an irradiation unit for applying a light or lights of wavelengths in the range of 0.6 to 2.4 microns;
   (d) a means for sensing the intensity of the light of a wavelength or wavelengths in the range of 0.6 to 2.4 microns applied to the reaction mixture in the absorption cell and transmitted thereby; and
   (e) a means for evaluating the change of absorbance or percent absorption of the reaction mixture for the light of the wavelength sensed in step (d) as a function of the reaction time, said evaluating means being operated in response to the sensing means.

29. The apparatus according to claim 28 wherein the insoluble carrier particles have an average diameter in the range of 0.1 to 1.0 micron.

30. The apparatus according to claim 28 wherein the insoluble carrier particles have an average diameter in the range of 0.2 to 0.8 micron.

31. The apparatus according to claim 28 wherein the absorption cell has a thickness of 1 to 5 mm.

32. The apparatus according to claim 28 wherein the windows of the cell which transmit the light are composed of transparent glass or synthetic resin having at least 30% transmittance for light of 0.6 to 2.4 microns in wavelength.

33. The apparatus according to claim 28 wherein the irradiation unit is designed to apply monochromatic or polychromatic light having a wavelength or wavelengths in the range of 0.8 to 1.8 microns.

34. The apparatus according to claim 28 wherein the absorption cell is equipped with an agitator.

* * * * *